United States Patent [19]
Bayley et al.

[11] Patent Number: 5,777,078
[45] Date of Patent: Jul. 7, 1998

[54] TRIGGERED PORE-FORMING AGENTS

[75] Inventors: Hagan Bayley, Grafton; Barbara J. Walker, Auburn; Chung-yu Chang, Worcester, all of Mass.; Brett Niblack, Nashville, Tenn.; Rekha Panchal, Shrewsbury, Mass.

[73] Assignee: Worcester Foundation for Experimental Biology, Shrewsbury, Mass.

[21] Appl. No.: 478,913

[22] Filed: Jun. 7, 1995

Related U.S. Application Data

[63] Continuation-in-part of Ser. No. 364,429, Dec. 27, 1994, which is a continuation of Ser. No. 54,898, Apr. 28, 1993, abandoned.

[51] Int. Cl.$^6$ .................... C07K 14/31; C07K 14/195
[52] U.S. Cl. .................... 530/350; 530/820; 530/825
[58] Field of Search .................... 530/350, 825, 530/820

[56] References Cited

U.S. PATENT DOCUMENTS 4,867,973  9/1989  Goers et al.
4,975,278  12/1990  Senter et al.

FOREIGN PATENT DOCUMENTS 0 185 076 B1  8/1992  European Pat. Off.
WO 94/25616  10/1994  WIPO

OTHER PUBLICATIONS

Adams et al., "Controlling Cell Chemistry with Caged Compounds", 1993, *Annu. Rev. Physiol.*, 55:755–84.
Avila et al., "A New Immunotoxin Built by Linking a Hemolytic Toxin to a Monoclonal Antibody Specific for Immature T Lymphocytes", 1988,*Int. J. Cancer*,42:568–71.
Avila et al., "A Carcinoembryonic Antigen–Directed Immunotoxin Built by Linking a Monoclonal Antibody to a Hemolytic Toxin", 1989, *Int. J. Cancer*,43:926–29.
Bayley, "Self-Assembling Biomolecular Materials in Medicine", 1994, *J. Cell. Biochem.*,56:168–70.
Bayley, "Channels With Single Transmembrane Segments", 1994, *News in Physiological Sciences*,9:45–46.
Bayley et al., "Photoactivatable Drugs", 1987, *Trends in Pharmacol. Sciences*,8:138–43.
Bayley, "Triggers and Switches in a Self-Assembling Pore-Forming Protein". 1994, *J. Cell. Biochem.*,56:177–82.
Bayley, "Novel Biomaterials: Genetically Engineered Pores", 1990, *Dept. of Energy Grant No. DE–FG02–9OR20018, Worcester Found. for Exptl. Biol.*.
Bowman, "Antibacterial Peptides: Key Components Needed in Immunity", 1991, *Cell*,65:205–207.
Chang et al., "A Photogenerated Pore–forming Protein", 1995, *Chem.& Biol.*,2(6):391–400.
Cheyley et al., "Type II Regulatory Subunits of cAMP–dependent Protein Kinase and their Binding PRoteins in the Nervous System of *Apolysia californica*", 1994, *J. Biol. Chem.*,269:2911–20

Chovnick et al., "A Recombinant Membrane Acting Immunotoxin", 1991, *Cancer Res.*,51:465–467.
Dawson et al., "Synthesis of Proteins by Native Chemical Ligation", 1994, *Science*,266:776–79.
Durell et al., "Theoretical Model of the Ion Channel Structure of Amyloid β–Protein ", 1994,*Biophys. J.*,67:2137–45.
Egholm et al., "PNA hybridizes to Complementary Oligonucleotides Obeying the Watson–Crick Hydrogen–bonding Rules", 1993, *Nature*,365:566–68.
Ellman et al., "Site–Specific Incorporation of Novel Backbone Structures into Proteins", 1992, *Science*255:197–200.
Goldmacher et al., "Photoactivation of Toxin Conjugates", 1992, *Bioconjugate Chem.*,3:104–107.
Gouaux et al., "Subunit Stoichiometry of Staphylococcal α–hemolysin in Crystals and on Membranes: A Heptameric Transmembrane Pore". 1994, *Proc. Natl. Acad. Sci. USA*, 91:12828–31.
Gray et al., "Primary Sequence of the Alpha Toxin Gene from Staphylococcus Aureus Wood 46", 1984, *Infect. Immun.*,46:615–618.
Hazum et al., "A Photocleavable Protecting Group for the Thiol Function of Cysteine", 1980, *Peptides*1980:*Proceedings of the Sixteenth European Peptide Symposium*,pp. 105–10.
Hilvert, "Extending the Chemistry of Enzymes and Abzymes", 1991, *Trends Biotechnol.*,9:11–17.
Huennekens, "Tumor Targeting: Activation of Prodrugs by Enzyme–Monoclonal Antibody Conjugates", 1994, *Trends Biotechnol.*,12:234–39.
Huston et al., "Protein Engineering of Single–Chain Fv Analogs and Fusion Proteins", 1991, *Methods in Enzymology*,203:46–89.
Kasianowicz et al., "Genetically Engineered Pores as Metal Ion Biosensors", 1994, *Mat. Res. Soc. Symp. Proc.*, 330:217–23.
Koltchine et al., "Homomeric Assemblies of NMDAR1 Splice Variants are Sensitive to Ethanol", 1993, *Neuroscience Letters*,152:13–16.
Krishnasastry et al., "Surface Labeling of Key Residues During Assembly of the Transmembrane Pore Formed by Staphylococcal α–Hemolysin", 1994, *Febs Letters*, 356:66–71.
Liotta et al., "Cancer Metastasis and Angiogenesis: An Imbalance of Positive and Negative Regulation", 1991, *Cell.*,64:327–36.
Lipkin, "Controlling Life's Gateway Opening and closing cell membranes on demand", 1994, *Science News*, 146:204–205.

(List continued on next page.)

*Primary Examiner*—Frank C. Eisenschenk
*Attorney, Agent, or Firm*—Fish & Richardson P.C.

[57] ABSTRACT

An inactive pore-forming agent which is activated to lytic function by a condition such as pH, light, heat, reducing potential, or metal ion concentration, or substance such as a protease, at the surface of a cell.

2 Claims, 13 Drawing Sheets

OTHER PUBLICATIONS

Maiti et al., Tolerogenic Conjugates of Xenogeneic Monoclonal Antibodies with Monomethoxypolyethylene Glycol. I. Induction . . . Xenogeneic Monoclonal Antibodies, 1988, *Int. J. Cancer*,3:17–22.

Marriott et al., Photomodulation of the Nucleating Activity of a Photocleavable Crosslinked Actin Dimer, 1992, *Biochemistry International*,26:943–951.

Murray, "Cyclin–dependent kinases: regulators of the cell cycle and more", 1994, *Chemistry&Biology*,1:191–195.

Nielsen et al., "Sequence–Selective Recognition of DNA by Strand Displacement with a Thymine–Substituted Polyamide", 1991, *Science*,254:1497–1500.

Noren et al., "A General Method for Site–Specific Incorporation of Unnatural Amino Acids into Proteins", 1989, *Science*,244:182–188.

Olejnik et al., "Photocleavable biotin derivatives: A versatile approach for the isolation of biomolecules", 1995, *Proc. Natl. Acad. Sci. USA*,92:7590–7594.

O'Reilly et al., "Angiostatin: A Novel Angiogenesis Inhibitor That Mediates the Suppression of Metastases by a Lewis Lung Carcinoma", 1994, *Cell*,79:315–328.

Panchal et al., "Differential Phosphorylation of Neuronal Substrates by Catalytic Subunits of Aplysia cAMP–dependent Protein Kinase with Alternative N Termini", 1994, *J. Biol. Chem.*,269:23722–23730.

Pastan et al., "Immunotoxins", 1986, *Cell*.47:641–648.

Pederzolli et al., "Biochemical and Cytotoxic Properties of Conjugates of Transferrin with Equinatoxin II, a Cytolysin from a Sea Anemone", 1995, *Bioconjugate Chem.*, 6:166–173.

Regen et al., "Supramolecular Surfactants: Amphiphilic Polymers Designed to Disrupt Lipid Membranes", 1989, *Biochem. and Biophysi. Res. Comm.*,159:566–571.

Senter et al., "Novel Photocleavable Protein Crosslinking Reagents and Their Use in the Preparation of Antibody–Toxin Conjugates", 1985, *Photochemistry and Photobiology*,42:231–237.

Stetler–Stevenson et al., "The Activation of Human Type IV Collagenase Proenzyme", 1989, *J. Biol. Chem.*, 264:1353–1356.

Thiele and Fahrenholz, "Photocleavable Biotinylated Ligands for Affinity Chromatography", 1994, *Analytical Biochemistry*, 218:330–337.

Thompson et al., "Photocleavable Nitrobenzyl–Protein Conjugates", 1994, *Biochem. and Biophysic. Res. Comm.*, 201:1213–1219.

Tobkes et al., "Secondary Structure and Assembly Mechanism of an Oligomeric Channel Protein", 1985, *Biochemistry*, 24:1915–1919.

Walker and Bayley, "Restoration of pore–forming activity in staphylococcal α–hemolysin by targeted covalent modification", 1995, *Protein Engineering*, 8:491–495.

Walker et al., "Genetically–Engineered Protease–Activated Triggers in a Pore–Forming Protein", 1994, *Mat. Res. Soc, Symp. Proc.*, 330:209–215.

Walker et al., "An intermediate in the assembly of a pore–forming protein trapped with a genetically–engineered switch", 1995, *Chemistry & Biology*, 2:99–105.

Walker et al., "A pore–forming protein with a metal–actuated switch", 1994, *Protein Engineering*, 7:655–662.

Walker et al., "A pore–forming protein with a protease–activated trigger", 1994, *Protein Engineering*, 7:91–97.

Walker et al., "Assembly of the Oligomeric Membrane Pore Formed by Staphylococcal α–Hemolysin Examined by Truncation Mutagenesis", 1992, *J. Biol. Chem.*, 267:21782–21786.

Walker et al., "Functional Expression of the α–Hemolysin of *Staphylococcus aureus* in Intact *Escherichia coli* and in Cell Lysates", 1992, *J. Biol. Chem.*, 267:10902–10909.

Walker et al., "Functional Complementation of Staphylococcal α–Hemolysin Fragments", 1993, *J. Biol. Chem.*, 268:5285–5292.

Wittung et al., "DNA–like double helix formed by peptide nucleic acid", 1994, *Nature*, 368:561–563.

Zorn et al., "Halothane acts on many potassium channels, including a minimal potassium channel", 1993, *Neuroscience Letters*, 161:81–84.

PCT International Search Report, PCT/US94/04016, mailed Jul. 8, 1994.

Chang et al., Chemistry and Biology, 1995, 2:391.

Amato, "Molecular Design Gets Into a Hole", 255:684 (1992).

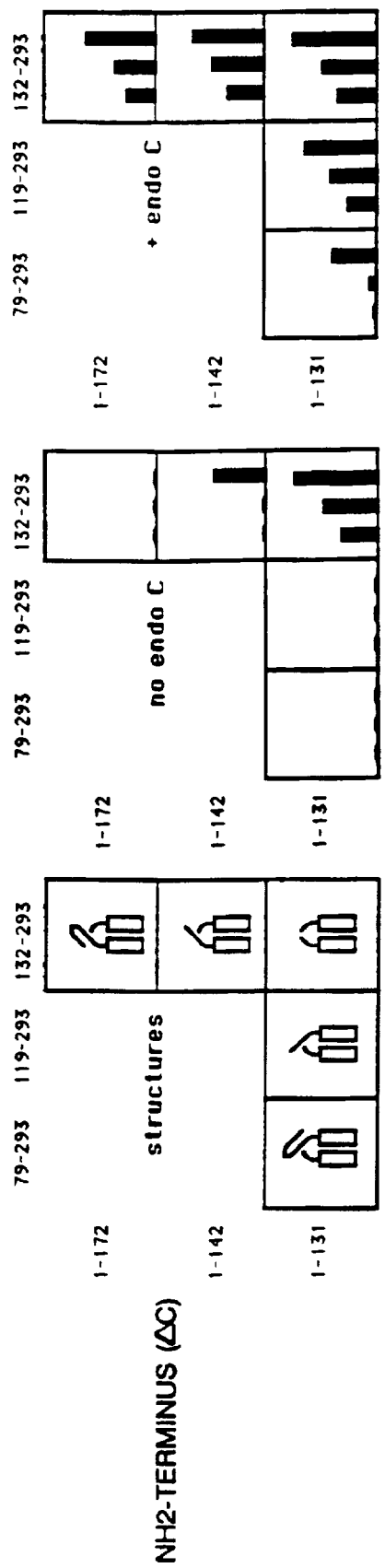

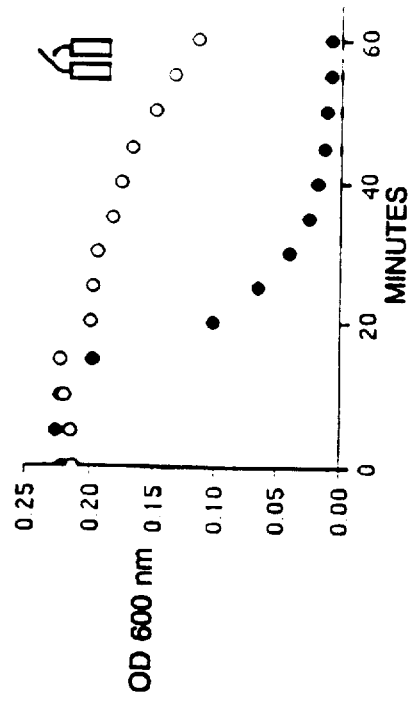
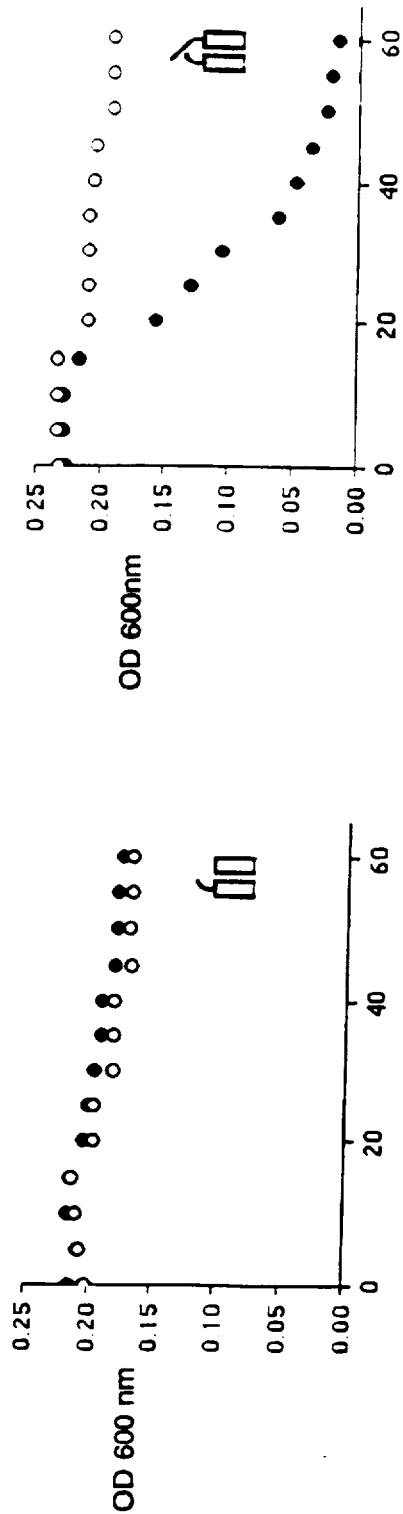
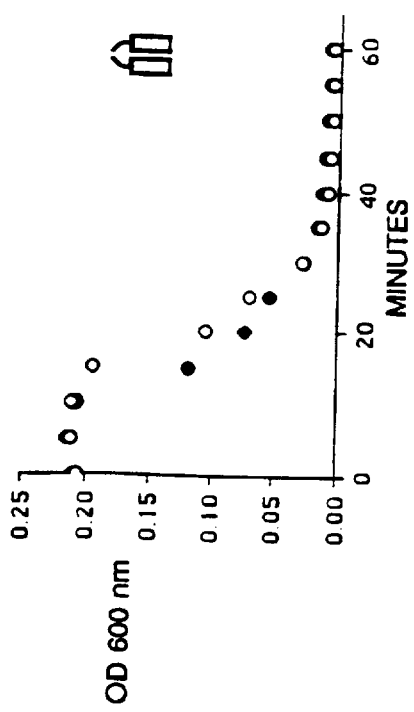
FIG. 2a  FIG. 2b  FIG. 2c  FIG. 2d

Screening methods

Primary screen: Two-chain library in a single plasmid with dual T7 promoters is screened by transfer to nitrocellulose, activation with tumor-cell extract, and hemolytic activity towards blood agar Secondary screen: IVTT of candidate plasmid, treat translation product with tumor-cell extract, add rRBCs and assay lysis

LIBRARY OF αHL MUTANTS based on a semi-random cassette encoding potential protease-activation site inactive

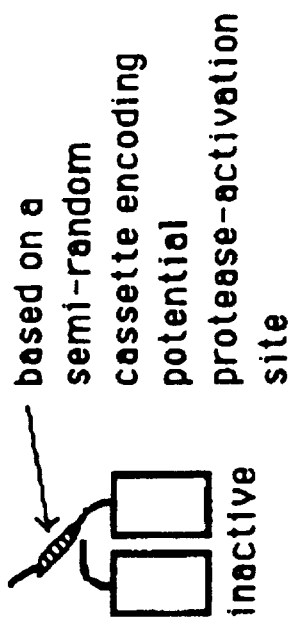

FIG. 11

R = peptide or protein

5,777,078

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 4 amino acids
      ( B ) TYPE: amino acid -continued ( C ) STRANDEDNESS: Not Relevant
( D ) TOPOLOGY: linear ( i i ) MOLECULE TYPE: protein ( x i ) SEQUENCE DESCRIPTION: SEQ ID NO:1:

Pro Leu Arg Pro
1

( 2 ) INFORMATION FOR SEQ ID NO:2:

( i ) SEQUENCE CHARACTERISTICS:
( A ) LENGTH: 4 amino acids
( B ) TYPE: amino acid
( C ) STRANDEDNESS: Not Relevant
( D ) TOPOLOGY: linear ( i i ) MOLECULE TYPE: protein ( x i ) SEQUENCE DESCRIPTION: SEQ ID NO:2:

Ser Ile Arg Cys
1

( 2 ) INFORMATION FOR SEQ ID NO:3:

( i ) SEQUENCE CHARACTERISTICS:
( A ) LENGTH: 4 amino acids
( B ) TYPE: amino acid
( C ) STRANDEDNESS: Not Relevant
( D ) TOPOLOGY: linear ( i i ) MOLECULE TYPE: protein ( x i ) SEQUENCE DESCRIPTION: SEQ ID NO:3:

Leu Pro Arg Lys
1

( 2 ) INFORMATION FOR SEQ ID NO:4:

( i ) SEQUENCE CHARACTERISTICS:
( A ) LENGTH: 4 amino acids
( B ) TYPE: amino acid
( C ) STRANDEDNESS: Not Relevant
( D ) TOPOLOGY: linear ( i i ) MOLECULE TYPE: protein ( x i ) SEQUENCE DESCRIPTION: SEQ ID NO:4:

Thr Met Arg Val
1

TRIGGERED PORE-FORMING AGENTS

This application is a continuation-in-part of U.S. Ser. No. 08/364,429, filed Dec. 27, 1994 which is a continuation of U.S. Ser. No. 08/059,898, filed Apr. 28, 1993 now abandoned.

STATEMENT AS TO FEDERALLY SPONSORED RESEARCH

This invention was made with Government support under Grant No. DE-FG02-90ER20018 awarded by the Department of Energy, co-sponsored by the Division of Energy Biosciences and the Division of Materials Sciences, Grant No. N00014-93-1-0962 awarded by the Office of Naval Research, and Grant No. R01 NS26760 awarded by the National Institutes of Health. The Government has certain rights in the invention.

FIELD OF THE INVENTION

This invention relates to pore-forming compounds.

BACKGROUND OF THE INVENTION

Transmembrane channels or pores can be formed by certain bacterial exotoxins (Bhakdi et al., Philos. Trans. R. Soc. Lond. B. Biol. Sci. 306:311–324, 1983). Pore-forming toxins, such as staphylococcal α-toxin (αHL), assemble into supramolecular amphiphilic polymers in the lipid bilayer of the cell membrane, thus generating stable transmembrane pores.

αHL, a single polypeptide chain of 33,200 daltons, is a water-soluble toxin secreted by *Staphylococcus aureus* (Gray et al., Infect. Immun. 46:615, 1984). αHL is capable of lysing erythrocytes in vitro by forming heptameric structures in the membranes of these cells (Gouaux et al., 1994, Proc. Natl. Acad. Sci. USA 91:12828–12831).

SUMMARY OF THE INVENTION

Despite developments in surgery, radiation therapy and chemotherapy, safe and effective treatments for many cancers has been elusive. Particularly recalcitrant to treatment are metastatic cells that remain after surgery or radiation therapy. These cells are often resistant to conventional chemotherapy.

The invention addresses this problem by providing a pore-forming compound which is active at the surface of the target cell. Limited pore formation can result in permeabilization of the cell membrane which can improve uptake of substances which are normally difficult to deliver into the cytoplasm of cells, such as cytotoxic chemotherapeutic agents or nucleic acids. Extensive pore formation can itself result in the destruction of the cell.

The invention features a chimeric compound composed of two components, each of which has a distinct function. One part of the chimera is a delivery agent which can be a cell-specific ligand capable of specifically binding to a molecule or structure on the surface of a target cell. This ligand is linked to an pore-forming agent which is capable of forming one or more pores in the lipid bilayer of a cell membrane which results in lysis or permeabilization of the cell.

The cell-specific ligand of the chimera, which can be synthetic or natural, may bind to a specific molecule or structure on the surface of a target cell, such as an antigen, growth factor receptor, or viral protein expressed on the surface of an infected cell. Preferably the ligand is an antibody. For therapeutic purposes, the cell-specific ligand or antibody can be one which binds to an unwanted cell in the body, such as a cell which is associated with a pathological condition. Such cells include but are not limited to tumor cells, cells which are chronically infected with virus, or cells, which when improperly regulated or expressed, result in a disease state, e.g., cells of the immune system. Unwanted cells may also be cells which express a recombinant therapeutic nucleic acid as a result of gene therapy. Elimination of such unwanted cells can be a means of regulating or stopping gene therapy.

Preferably, the pore-forming agent, which is capable of forming one or more lytic pores in a target cell, is a bacterial exotoxin, including but not limited to αHL, aerolysin, perfringolysin, pneumolysin, streptolysin O, listeriolysin, *Bacillus thuringensis* toxin, or an *E. coli*-derived lytic molecules such as hemolysin or colicin, or an agent derived from a eucaryotic cell, such as a defensin, magainin, mellitin, complement, perforin, yeast killer toxin or histolysin.

The two components of the chimeric compound are linked via a non-covalent or covalent bond, or both. Preferably the linkage is a covalent bond involving a sulfur atom, more preferably a disulfide, thioester or thioether bond. The compound of the invention can also be produced as a recombinant fusion protein with the two components of the chimera linked by a peptide bond.

The invention also features a mutant pore-forming agent that is inactive, but able to be converted to an active lytic form by conditions or substances at the surface of a target cell as well as a chimeric compound comprising such an activatable agent linked to a cell-specific ligand. Such a molecule may be activated physically, chemically or biochemically. Physical conditions capable of activating the compound of the invention include but are not limited to the presence of heat or light. The inactive pore-forming agent may also be activated by a conformational change induced by the act of the inactive pore-forming agent binding to its ligand on the surface of the target cell. Chemical conditions capable of activating the pore-forming agent include a change in pH, reduction potential or concentration of metal ions. Biochemical substances, specifically associated with the target cell and capable of activating the compound, include but are not limited to proteases, esterases, glycosidases, ectokinases, or phosphatases. These substances or conditions at the cell surface may be endogenous, e.g., secreted by the target cell, such as a tumor protease, or exogenous, e.g. provided by a source other than the target cell, such as a light emitted from a lamp or fiber-optic device. For example, a therapeutic treatment can comprise topical application of a compound or agent of the invention to a skin tumor and activation by exposure to a light source.

The invention also includes an inactive pore-forming agent that is activated by light. A photoactivatable pore-forming agent preferably contains at least one cysteine which is linked to an α-carboxy-2-nitrobenzyl (CNB) group. Photoactivation of the agent to lytic activity takes place when the CNB group is removed from the agent by irradiation at a wavelength of at least 300 nm. Preferably the agent is a single cysteine mutant of αHL. More preferably, the agent is selected from a group of mutants consisting of R104C, E111C, K168C, and D183C, and most preferably the agent is the αHL mutant R104C.

The invention also features a water-soluble compound, e.g., 2-bromo-2-(nitrophenyl)acetic acid (BPNA), having the formula:

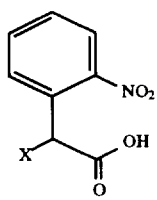

where X represents a halogen. The halogen is preferably bromine, but may be iodine. X may also represent other leaving groups, e.g., aryl or alkyl sulfonates. BPNA is capable of modifying a sulfhydryl-containing molecule, e.g., a cysteine-containing polypeptide, with a photolysable α-carboxy-2-nitrobenzyl (CNB) group. The α-carboxy substituent both increases the solubility of the reagent at physiological pH values and increases the reactivity toward nucleophilic attack. This substituent may be replaced with sulfonate or tetraalkyl ammonium substituents. The invention also include a method of labelling proteins or polypeptide with a photolysable CNB group using BPNA.

Any water-soluble protein or polypeptide can be modified using BPNA. Proteins or polypeptides can be modified on one or several cysteines. Photoactivatable pore-forming agents have been made by modifying αHL with BPNA. An active single-cysteine mutant of αHL is inactivated by reaction with BNPA. When the CNB group, which is introduced by BNPA treatment, is removed by photolysis, pore-forming activity is restored.

Also within the invention is an inactive pore-forming agent that is activated by an enzyme. An enzyme-activated pore-forming agent preferably contains an amino acid extension in an internal domain, e.g., in a glycine-rich loop of an internal domain, of the agent. By the term "internal domain" is meant a domain of a pore-forming agent which does not contain either the amino-terminus or carboxy-terminus of the protein. By the term "glycine-rich loop" is meant a portion of a pore-forming protein 10 to 100 amino acids in length, at least 10% of which are the amino acid glycine. For example, the glycine-rich loop of αHL spans amino acids 111 to 150 and is 20% glycine. By amino acid extension is meant the addition of a peptide of one or more amino acids to the pore-forming agent The amino acid extension contains at least one amino acid, preferably at least 10 amino acids, more preferably at least 40 amino acids, and most preferably, the extension contains a cell-specific ligand, e.g., the antigen-binding domain of an antibody. Preferably, the amino acid extension is cleaved off by the enzyme to restore lytic activity to the pore-forming agent.

The enzyme-activated pore-forming agent of the invention may be an overlap mutant of staphylococcal α-toxin. In preferred embodiments, the enzyme is endoproteinase Lys-C (endo C), the amino acid extension contains a lysine residue, and the agent is K8A(1-142●132-293) or K8A(1-172●132-293). Alternatively, the enzyme is clostripain, the amino acid extension contains an arginine residue, and the agent is K8A,K131R(1-142●132-293) or K8A,K131R(1-142●132-293). The enzyme may also be a cell-specific protease, such as an enzyme secreted by tumor cells. Most preferably, the inactive pore-forming agents are activated by the tumor-specific protease, cathepsin B, e.g., K8A,G130R,K131R(1-172●132-293) or K8A,G130R,K131R(1-131●119-293).

The invention also includes metal-sensitive pore-forming agents that are activated by a change in metal ion concentration. Preferably the metal-sensitive agent contains an amino acid substitution in an internal domain, e.g., in a glycine-rich loop of an internal domain, of the agent. Most preferably, the metal-activated agent is αHL-H5m and is inactivated by the presence of divalent metal ions, e.g., $Zn^{2+}$ and activated by the presence of a chelating agent, e.g., EDTA. The invention also includes inactive pore-forming agents that are activated by the presence of divalent metal ions.

The compound of the invention can be used to treat animals, preferably humans, to destroy unwanted cells associated with a pathological condition. Both the activatable pore-forming agent alone and the chimeric compound of the invention can be administered in a pharmaceutically acceptable carrier for therapeutic use. Unwanted cells, in an animal or removed from an animal, can be destroyed by contacting the target cells with the compound of the invention either alone or together with a chemotherapeutic agent. Inactive pore-forming agents alone can be used to block natural target cells prior to administration of the chimeric compounds of the invention, i.e., immunolysin therapy.

The compound of the invention and a chemotherapeutic agent may be administered simultaneously or sequentially. A chemotherapeutic agent is defined as a compound or nucleic acid which is cytotoxic to a cell, such as mechloroethamine, cyclophosphamide, ifosfamide, L-sarcolysin, chlorambucil, hexamethylmelamine, thiotepa, busulfan, carmustine, lomustine, semustine, streptozocin, dacarbazine, methotrexate, fluorouracil, cytarabine, mercaptopurine, thioguanine, pentostatin, vinblastine, vincristine, etoposide, teniposide, actinomycin D, daunomycin, doxorubicin, bleomycin, plicamycin, mitomycin, cisplatin, mitoxantrone, hydroxyurea, procarbozine, mitotane, aminoglutethimide, prednisone, hydroxyprogesterone, diethylstilbestrol, tamoxifen, flutamide, or leuprolide, as well as a DNA oligonucleotide, which is complementary to an essential gene of a cell and capable of eliminating or down-regulating expression of such a gene, or a ribozyme which can disrupt protein synthesis of a cell. A peptide-nucleic acid (PNA), i.e., a peptide backbone substituted with nucleic acid bases (Wittung et al., 1994, Nature 368:561–563), may also be co-administered. PNA binds to DNA more tightly than DNA oligonucleotides, in some cases causing strand displacement on double-stranded DNA.

The invention also features a method of screening pore-forming compounds for the ability to be activated by a condition or substance associated with a target cell. The candidate compound can be generated by combinatorial mutagenesis of a site involved in interaction with a cell-specific condition or substance. Preferably, target cells are contacted with a candidate compound in the presence and absence of a cell-specific condition or substance and cytolysis evaluated as an indication that the candidate compound is activatable.

Other features and advantages of the invention will be apparent from the following description of the preferred embodiments thereof, and from the claims.

DETAILED DESCRIPTION

The drawings are first briefly described.

Drawings FIGS. 1a–1c are of graphs showing activation of hemolytic activity in overlap mutants of αHL by proteases treatment. A key to structures of two-chain αHL complementation mutants produced by coupled in vitro transcription/translation (IVTT) is shown in the left panel. The center and right panels show the results of a microtiter assay using two-fold serial dilutions. Assays of mutants which have not been treated with protease are shown in the center graph and assays of replicate samples after treatment with endoproteinase Lys-C (endo C) are shown in the right graph. In each window, the tops of the bars indicate the well with 50% hemolysis after 1 h, 3 h and 24 h (left to right). The top of each window represents well 12 and the bottom well "0" ("0" denotes no hemolysis in well 1). The vertical scale is logarithmic to the base 2. Overlap mutants were activated by adding endo C (1.0 µg) to the IVTT mix (10 µL). The initial dilution of the IVTT mix in well 1 was 1:4. The individual polypeptides that make up the two-chain mutants have no hemolytic activity.

FIGS. 2a–2d are a set of graphs showing hemolysis by selected mutants as determined by a spectrophotometric assay. The decrease in light scattered at 600 nm, an indication of erythrocyte lysis, was monitored after the addition of IVTT mix (10 µL, before additions) to 0.025% rabbit erythrocytes (500 µL). The mutants used are as in FIGS. 1a–1c, with the addition of the non-activatable gap mutant αHL(1-131)●(143-293) as a control (bottom left panel).

FIGS. 3a–3b are photographs of endo-C-treated proteolytic fragments of overlap mutants and their component polypeptides separated using sodium dodecylsulfate-polyacrylamide gel electrophoresis (SDS-PAGE). FIG. 3A shows untreated individual chains and the FIG. 3b shows individual chains treated with endo C (1 µg added to 6 µL IVTT mix).

FIGS. 4a–4b are photographs of an SDS-PAGE gel showing the results of treatment of the two-chain mutants with endo C. FIG. 4a shows untreated two-chain mutants and FIG. 4b shows two-chain mutants treated with endo C (1 µg added to 12 µL IVTT mix). The two-chain mutants are converted to fragments that co-migrate with polypeptides 1-131 and 132-293. These fragments are resistant to further breakdown. In the cases of mutants with forward overlaps, a full-length αHL polypeptide is also generated.

FIG. 5 is a schematic interpretation of the proteolysis data. The final state of both forward and reverse overlap mutants is boxed.

FIGS. 6a–6b are photographs of a SDS-PAGE gel showing the time course of proteolysis of the overlap mutant K8A (1-172)●(132-293) with endo C (right). Proteolysis results in the formation of two chains, 1-131 (open arrow) and 132-293 (closed arrow) without further degradation. IVTT mix (12.5 µL), produced using ($^{35}$S)methionine at 1200 Ci/mmol, was treated with endo C (1.0 µg) at 30° C. Aliquots were removed after designated times and treated with 1 mM Nα-p-tosyl-L-lysine chloromethyl ketone (TLCK). Proteolysis of single-chain K8A was performed as a control (left).

FIG. 7a is a diagram of αHL overlap mutants and FIGS. 7b–7c are graphs showing selective proteolytic activation of αHL 1-172●132-293 overlap mutants containing Lys-131 or Arg-131. Rabbit erythrocyte hemolysis was monitored by the decrease in light scattering at 600 nm after the addition of IVTT mix to a suspension of rabbit erythrocytes. FIG. 7b shows the results after endo C activation and the FIG. 7c shows the results after clostripain activation.

FIG. 8 is a graph showing the results of a spectrophotometric assay for hemolysis by αHL-H5m in the presence or absence of 10 µM ZnSO$_4$. The decrease in light scattered at 600 nm was monitored after the addition of purified αHL-H5m (0.4 mg/ml, 1.0 µL) to 0.025% rabbit erythrocytes (500 µL). The assay was carried out at room temperature with rabbit erythrocytes diluted to 0.025% in 20 mM K-phosphate, 150 mM NaCl, pH 7.4.

FIG. 11 is a diagram showing the method of screening a combinatorial library for pore forming agents which are activated by cell-specific substances.

Figure 13:
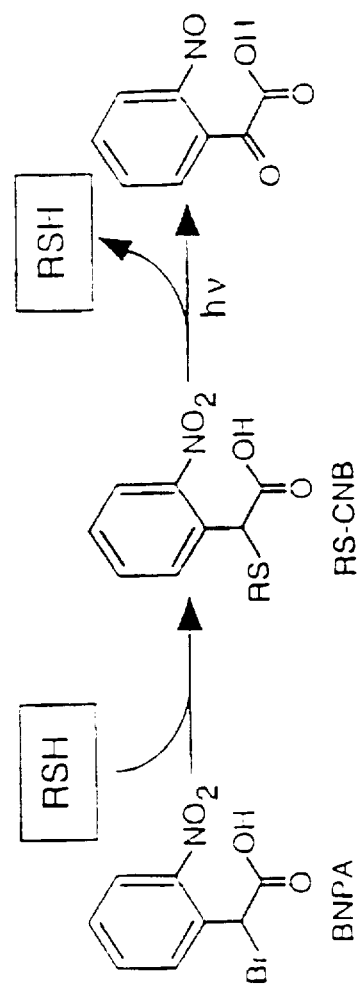

FIG. 13 is a diagram showing the formation of CNB-thioethers and their proposed photochemistry. Cysteine-containing peptides and proteins can be selectively modified with BNPA in aqueous buffers at pH 8.5. The CNB group is removed by irradiation at wavelengths ($\geq$300 nm) that do little damage to biological samples.

Figure 14:
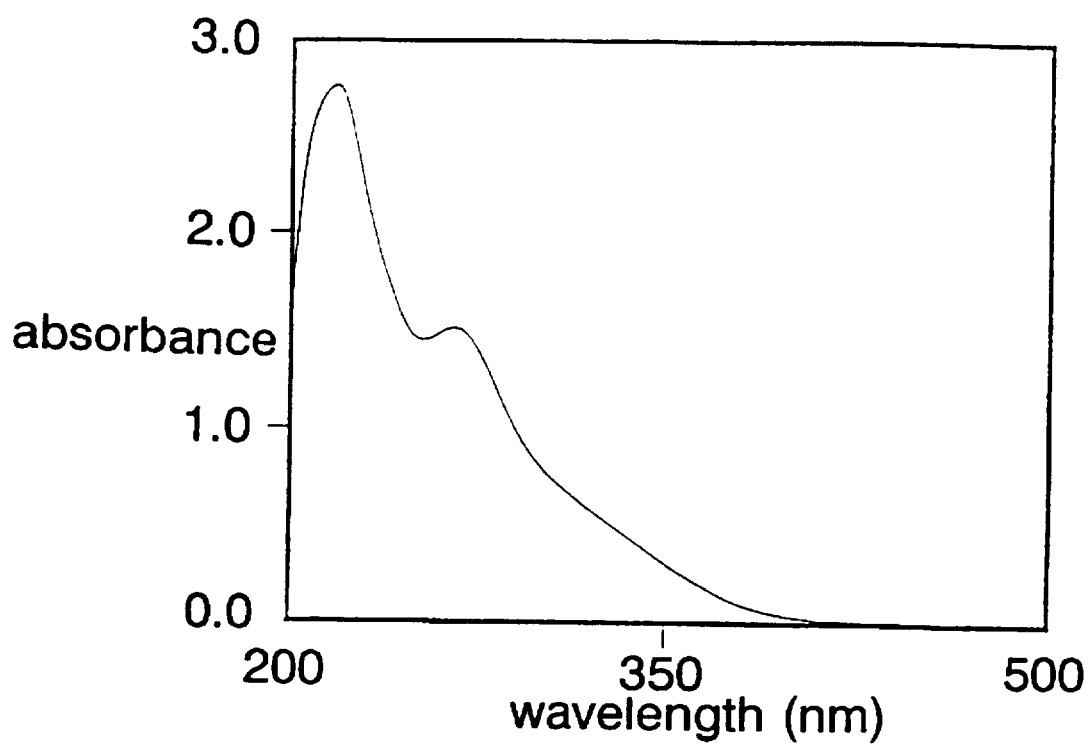

FIG. 14 is a line graph showing a UV spectrum of GS-CNB, the BNPA adduct of glutathione. The GS-CNB was 330 µM (based on amino acid analysis) in 10 mM NaP$_i$, pH 8.5.

Figure 15:
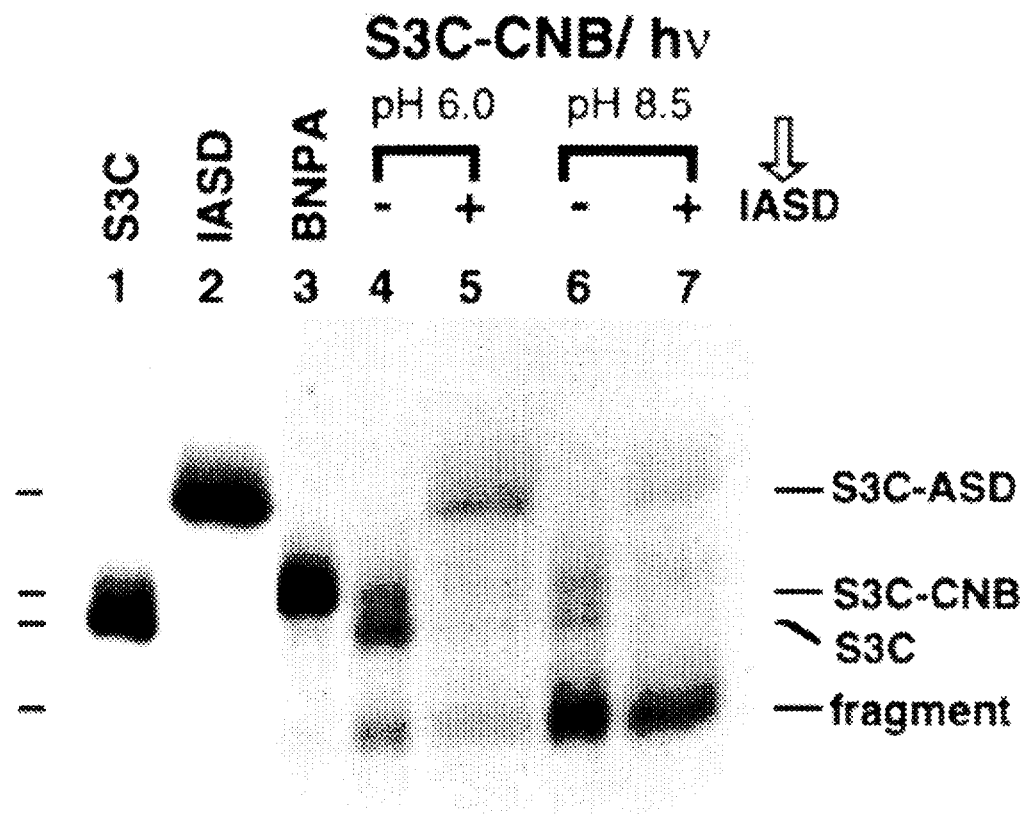

FIG. 15 is a photograph of an autoradiogram showing the chemical modification of αHL-S3C. Modifications by the charged reagents result in characteristic gel shifts after extended electrophoresis. $^{35}$S-labeled S3C was treated and subjected to electrophoresis in a 12% SDS polyacrylamide gel. An autoradiogram of a region between the 29.5 kDa and 45.5 kDa molecular weight markers is shown. Lane 1, untreated S3C; lane 2, S3C treated with 4-acetamido-4'-(iodoacetyl)amino)stilbene-2,2'-disulfonate (IASD); lane 3, S3C treated with BNPA; lane 4, BNPA adduct of S3C photolysed at pH 6.0; lane 5, BNPA adduct of S3C photolysed at pH 6.0 after the photolysis products were further treated with IASD; lane 6, BNPA adduct of S3C photolysed at pH 8.5; lane 7, BNPA adduct of S3C photolysed at pH 8.5 after the photolysis products were further treated with IASD. "S3C" represents αHL-S3C; "S3C-CNB" represents S3C adduct formed by reaction of Cys-3 with BNPA; "S3C-ASD" represents S3C adduct formed by reaction of Cys-3 with IASD.

Figure 16:
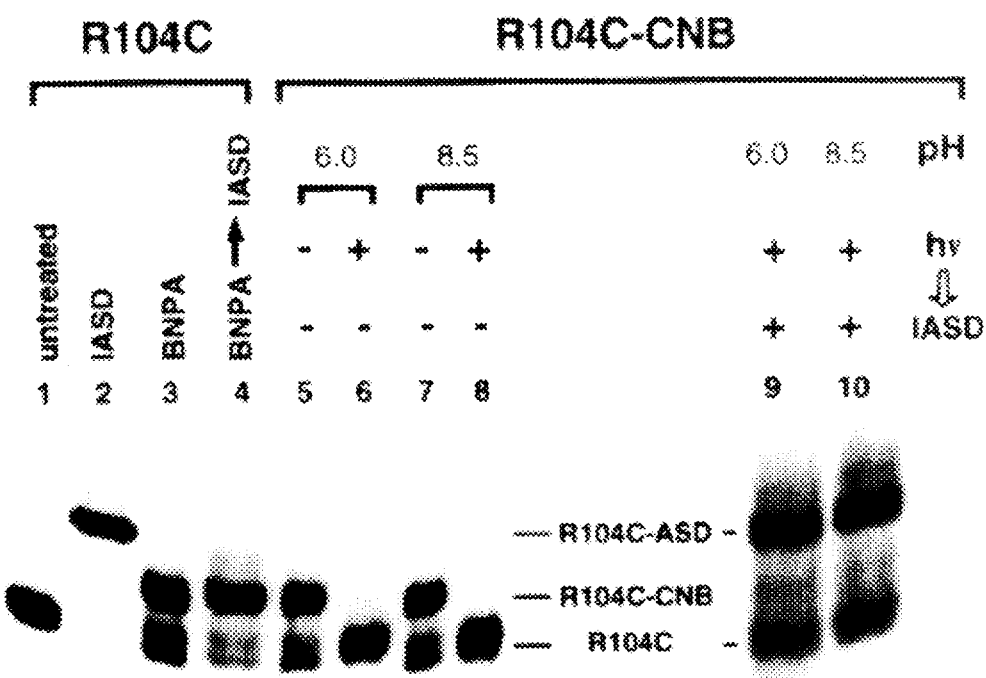

FIG. 16 is a photograph of an autoradiogram showing chemical modification of αHL-R104C. $^{35}$S-labeled R104C was treated and subjected to electrophoresis in a 12% SDS polyacrylamide gel. An autoradiogram of a region between of the 29.5 kDa and 45.5 kDa markers is shown. Lane 1, R104C; lane 2, R104C treated with IASD; lane 3, R104C treated with BNPA; lane 4 R104C treated with BNPA and further treated with IASD; lane 5, BNPA adduct of R104C after removal of excess reagent; lane 6, BNPA adduct of R104C after removal of excess reagent photolysed at pH 6.0; lane 7, BNPA adduct of R104C after removal of excess reagent; lane 8, BNPA adduct of R104C after removal of excess reagent photolysed at pH 8.5; lane 9, BNPA adduct of R104C after removal of excess reagent photolysed at pH 6.0 after the photolysis products were further treated with IASD. "R104C" represents αHL-R104C; "R104C-CNB" represents adduct formed by reaction of Cys-104 with BNPA; "R104C-ASD" represents R104C adduct formed by reaction of Cys-104 with IASD.

Figure 17:
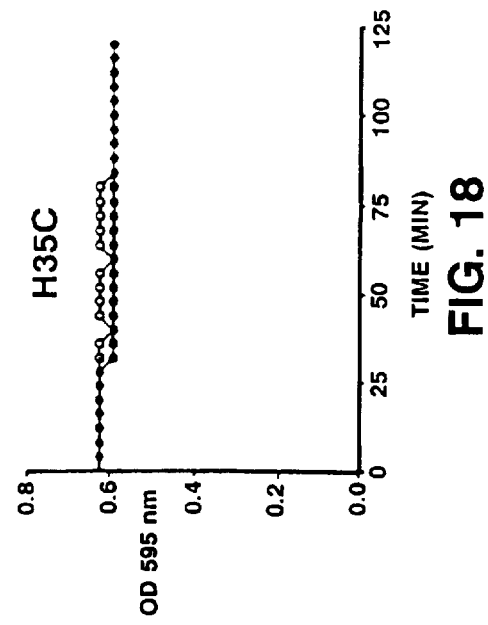

FIG. 17 is a line graph showing the results of irradiation of the wild type α-HL, K8A, at 300 nm. K8A was prepared by IVTT and treated with BNPA. Excess reagent was removed by repeated ultrafiltration. K8A was irradiated at 300 nm (●) or left untreated (○). Lysis of rabbit erythrocytes was then measured by monitoring light scattering at 595 nm. The concentration of protein in the assay was 0.5 µg/ml.

Figure 18:
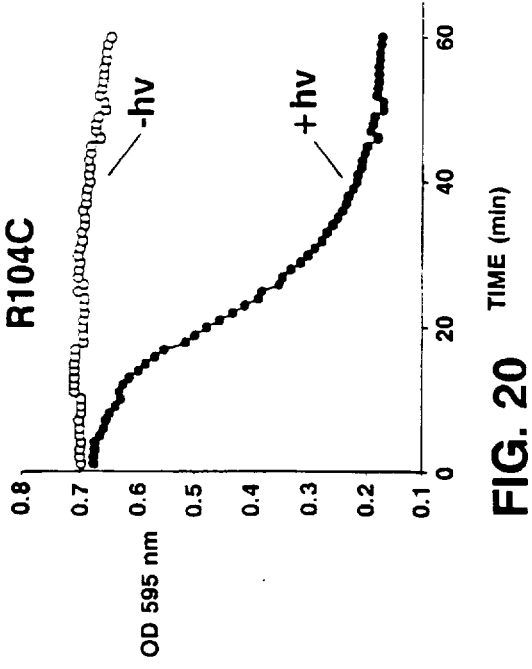

FIG. 18 is a line graph showing the results of irradiation of the α-HL, H35C, at 300 nm. H35C was prepared by IVTT and treated with BNPA. Excess reagent was removed by repeated ultrafiltration. H35C was irradiated at 300 nm (●) or left untreated (○). Lysis of rabbit erythrocytes was then measured by monitoring light scattering at 595 nm. The concentration of protein in the assay was 0.5 µg/ml.

Figure 19:
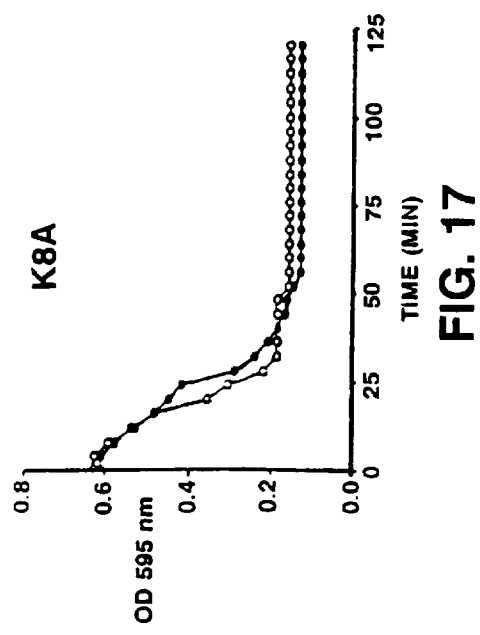

FIG. 19 is a line graph showing activation of the α-HL, R104C, by irradiation at 300 nm. R104C was prepared by IVTT and treated with BNPA. Excess reagent was removed by repeated ultrafiltration. R104C was irradiated at 300 nm (●) or left untreated (○). Lysis of rabbit erythrocytes was then measured by monitoring light scattering at 595 nm. The concentration of protein in the assay was 0.5 µg/ml.

Figure 20:
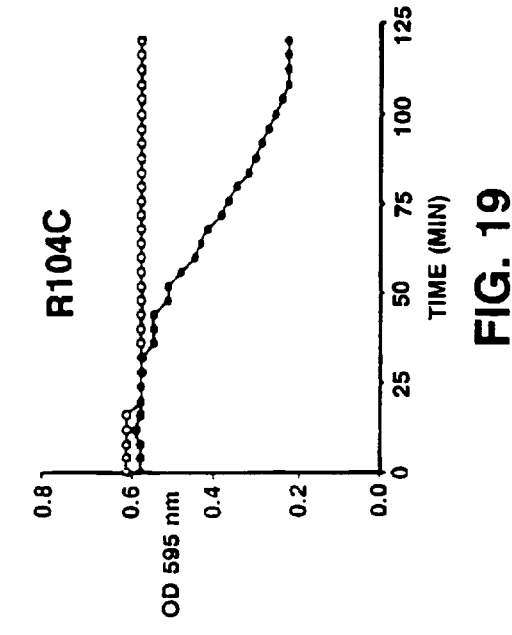

FIG. 20 is a line graph showing activation of αHL-R104C-CNB prepared from purified R104C. R104C prepared by expression in S. aureus was modified with BNPA. Excess reagent was removed by gel filtration. αHL-R104C-CNB was irradiated at 300 nm (●) or left untreated (○). Hemolytic activity (lysis of rabbit erythrocytes) was measured by monitoring light scattering at 595 nm. The concentration of R104C in the assay was 2.0 µg/ml.

COMPOUNDS OF THE INVENTION

As described in the Summary above, the compound of the invention employs several components which will now be discussed in greater detail.

One component of the compound of the invention is a lytic pore-forming agent, which can be naturally-occurring or synthetically-made. The pore-forming agent can be a molecule as well as a fragment, derivative or analog of such a molecule, which is capable of generating one or more transmembrane pores in the lipid bilayer of a cell which results in the lysis or permeabilization of the cell. Such pore-forming agents derived from bacteria include αHL, E. coli hemolysin, E. coli colicin, B. thuringenis toxin, aerolysin, perfringolysin, pneumolysin, streptolysin O, and listeriolysin. Eucaryotic pore-forming agents capable of lysing cells include defensin, magainin, mellitin, complement, perforin, yeast killer toxin and histolysin. Synthetic organic molecules, such as Pederson's crown ethers and valinomycin, which are capable of forming a lytic pore in a cell membrane can also be used. Other synthetic lytic pore-forming agents are described in Regen et al., Biochem. Biophys. Res. Commun. 159: 566–571, 1989.

The compound of the invention can also include fragments of naturally-occurring or synthetic pore-forming agents which exhibit lytic activity. In addition to substantially full-length polypeptides, the present invention provides for biologically active fragments of the polypeptides. A pore-forming polypeptide or fragment is biologically active if it is capable of forming one or more lytic pores in natural or synthetically-made lipid bilayers.

Also within the invention is an inactive pore-forming agent of the invention which is incapable of forming pores in natural or synthetically-made lipid bilayers until a substance or condition at the surface of the target cell acts upon it to convert it into an active lytic form. The invention encompasses the mutant inactive pore-forming agent alone as well as linked to a cell-specific ligand.

Biologically active fragments of lytic pore-forming agents can be generated by methods known to those skilled in the art, e.g., proteolytic cleavage or expression of recombinant peptides. The ability of a candidate fragment to permeabilize cell membranes can be assessed by methods known to those skilled in the art, e.g., by the release of intracellular contents, such as ATP or radioactive label from pre-loaded cells or by the uptake of a dye, such as trypan blue which is excluded by intact cells.

As used herein, the term "fragment or segment", as applied to a polypeptide, is at least 5 contiguous amino acids. In the invention, fragments are typically at least 10 contiguous amino acids, more typically at least 20 contiguous amino acids, usually at least 30 contiguous amino acids, preferably at least 40 contiguous amino acids, more preferably at least 50 contiguous amino acids, and most preferably at least 60 to 80 or more contiguous amino acids in length.

The present invention also provides for analogs of naturally-occurring pore-forming agents which can lyse cells. Analogs can differ from naturally-occurring pore-forming agents by amino acid sequence differences or by modifications which do not affect sequence, or by both.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to enzymes which affect glycosylation e.g., mammalian glycosylating or deglycosylating enzymes. Also included are peptides which have phosphorylated amino acid residues, e.g., phosphotyrosine, phosphoserine, or phosphothreonine or have been modified to add fatty acids.

The invention also includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic can result in a more stable peptide and thus, in most cases, a more useful therapeutic agent. Such mimetics, and methods of incorporating them into polypeptides, are well known in the art. Similarly, the replacement of an L-amino acid residues is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Although most modifications are designed to make proteins more resistant to proteolytic degradation, the invention also embraces modifications which enhance such degradation, for the purpose of rapidly eliminating free compound which is not bound to a target cell, thus minimizing therapeutic complications.

Since antibodies to bacterial toxins may exist in patients as a result of previous immunization, infection or treatment with toxin-based therapeutic agents, modifications to render the compound non-immunogenic e.g., by coupling to monomethoxy-polyethylene glycol (mPEG) (Sehon et al., Int. Arch. of Allergy and Immunol. 94:11–20, 1991) are also included.

The invention also includes modifications which result in an inactive pore-forming agent which can be specifically activated by a cell-associated substance or condition. Such a modification can be the addition of a peptide containing an enzymatic cleavage site, e.g., lysine or arginine residues, the peptide bonds of which are hydrolyzed by the enzyme trypsin. Other modifications, such as the addition of a chemically-reactive group or photoactivated group are also included in the invention.

Addition of a metal binding site e.g., by the addition of histidine, cysteine or unnatural amino acids, such as 1,2, triazole-3-alanine and 2-methyl histidine, which have altered $PK_a$ values, steric properties, and arrangement of N atoms resulting in different abilities to bind metal ions, are also included in the invention.

Also included are peptides which have been modified so as to optimize solubility properties or to mediate activation by a cell-associated substance. Analogs can differ from naturally occurring agents by alterations of their primary amino acid sequence. These peptides include genetic variants, both natural and induced. Induced mutants can be made by various techniques, e.g., by random mutagenesis of the encoding nucleic acids using irradiation or exposure to ethyl methanesulfonate (EMS), or by site-specific mutagenesis or other techniques of molecular biology, such as polymerase chain reaction (PCR). Also included are analogs which include residues other than naturally occurring L-amino acids, e.g., D-amino acids, non-naturally occurring or synthetic amino acids, e.g., β or γ amino acids, or L-amino acids with non-natural side chains using known methods. Methods for site-specific incorporation of non-natural amino acids into the protein backbone of proteins are described in Ellman et al., Science 255:197, 1992. The peptides of the invention are not limited to products of any of the specific exemplary process listed herein.

Useful mutants can be identified using the inventive screening assay, in which a combinatorial library containing a semi-random mutational cassette is screened for activity or the ability to be activated by a condition or substance.

Cell-specific ligands

The delivery portion or cell-specific ligand of the compound can be any ligand which binds specifically to the target cell. The invention can employ not only intact monoclonal or polyclonal antibodies, but also an immunologically-active antibody fragment, such as a Fab' or (Fab')$_2$ fragment, or a genetically engineered Fv fragment (Ladner et al., U.S. Pat. No. 4,946,788).

Delivery agents can also include other cell-specific ligands, e.g., hormones such as steroid hormones, or peptide hormones; neuroactive substances, e.g., opioid peptides; insulin; growth factors, e.g., epidermal growth factor, insulin-like growth factor, fibroblast growth factor, platelet derived growth factor, tumor necrosis factor; cytokines, e.g., an interleukin (IL), e.g., IL-2, IL-4, or IL-5; melanocyte stimulating hormone; a substance or receptor which has affinity for a particular class of cells (or viruses) e.g., cancer cells, virally infected cells, immune cells, e.g., B cells or T cells or a subset thereof, e.g., soluble fragments of CD4, which bind to the protein gp120 expressed on HIV-infected cells; or a substance with an affinity for a class of molecules, e.g., a lectin, e.g., concanavalin A, which binds a subset of glycoproteins. Adhesion molecules, e.g., molecules expressed on cells of hematopoetic origin, such as CD2, CD4, CD8 which are expressed on T cells, selecting, integrins, as well as adhesion molecules expressed on non-immmune cells, may also be used as delivery agents to direct the compound of the invention to target cells. Since some cancer cells abnormally express certain adhesion molecules, receptors for such adhesion molecules may also be used as delivery agents.

Linkage of lytic pore-forming agents to cell-specific ligands

The two functional components of the compound of the invention are linked together via a covalent or non-covalent bond, or both. Non-covalent interactions can be ionic, hydrophobic, or hydrophilic, such as interactions involved in a leucine-zipper or antibody-Protein G interaction (Derrick et al., Nature 359:752, 1992).

A covalent linkage may take the form of a disulfide bond. The DNA encoding one of the components can be engineered to contain a unique cysteine codon. The second component can be derivatized with a sulfhydryl group reactive with the cysteine of the first component. Alternatively, a sulfhydryl group, either by itself or as part of a cysteine residue, can be introduced using solid phase polypeptide techniques. For example, the introduction of sulfhydryl groups into peptides is described by Hiskey (Peptides 3:137, 1981).

Proteins can be chemically modified by standard techniques to add a sulfhydryl group. For example, Traut's reagent (2-iminothiolane-HCl) (Pierce Chemicals, Rockford, Ill.) can be used to introduce a sulfhydryl group on primary amines, such as lysine residues or N-terminal amines. A protein or peptide modified with Traut's reagent can then react with a protein or peptide which has been modified with reagents such as N-succinimidyl 3-(2-pyridyldithio) propionate (SPDP) or succinimidyl 4-(N-maleimidomethyl)cyclohexane-1-carboxylate (SMCC) (Pierce Chemicals, Rockford, Ill.).

A free sulfhydryl group of an antibody may be generated using methods known to the art. For example, the antibody can be enzymatically cleaved with pepsin to yield (Fab')$_2$ fragments, which are then gently reduced with dithiothreitol (DTT) or 2-mercaptoethanol to yield free sulfhydryl-group-containing Fab' fragments. Antibody fragments, e.g., single chain Fv, can also be expressed recombinantly and genetically engineered to contain a terminal cysteine group using methods known to the art or chemically modified as described above.

Once the correct sulfhydryl groups are present on each component of the compound, the two components are purified, sulfur groups on each component are reduced; the components are mixed; and disulfide bond formation is allowed to proceed to completion at room temperature. To improve the efficiency of the coupling reaction, the cysteine residue of one of the components, e.g., cysteine-αHL, can be activated prior to addition to the reaction mixture with 5,5'-dithiobis(2-nitrobenzoic) acid (DTNB) or 2,2'-dithiopyridine, using methods known to the art. Following the reaction, the mixture is dialyzed against phosphate buffered saline to remove unconjugated molecules. Sephadex chromatography or the like is then carried out to separate the compound of the invention from its constituent parts on the basis of size.

The components of the chimera can also be joined using the polymer, monomethoxy-polyethylene glycol (mPEG), as described in Maiti et al., Int. J. Cancer Suppl. 3:17–22, 1988.

If the compound of the invention is produced by expression of a fused gene, a peptide bond serves as the link between the pore-forming agent and the cell-specific ligand. For example, a recombinant fusion protein of a single chain Fv fragment of an antibody and a pore-forming agent can be made according to methods known in the art, e.g., Huston et al., Meth. Enzymol. 203:46–88, 1991.

Activating conditions or substances

An inactive compound of the invention can be activated at the surface of the target cell by certain conditions or substances. These conditions or substances may be endogenously provided by the cell itself or exogenously provided by a source other than the target cell. Physical, chemical or biochemical conditions can activate lytic activity. Such conditions may activate the compound of the invention by inducing a conformational change in one or both of the components of the chimera. Any physical condition, such as a heat or light at the surface of the target cell can be used to activate the compound of the invention. Since temperature increases and changes in pH have been associated with certain tumor cells compared to normal cells, a heat-sensitive or pH-sensitive moiety can be used to confer the ability to be activated by such cells.

In another example, a compound of the invention which is activatable by light can be particularly useful for the purging of unwanted leukemic cells from blood by transiently exposing blood to light via a UV-emitting extracorporeal device. Accessible tumors such as skin cancers can also be treated in this manner, and relatively inaccessible tumors, such as lung cancers, can be reached using light emissions from fiber optic devices.

Chemical conditions, such as pH, reducing potential or the presence of metal ions, may also serve as activators. For example, the compound of the invention can be modified to contain a protecting group which is altered or removed by exposure to a chemical condition at the surface of the target cell, thus resulting in the activation of lytic activity.

Since metastatic cancer cells have been shown to secrete matrix metalloproteinases (Liotta et al., Cell 64:327–336, 1991), a metalloproteinase recognition site that has been incorporated into the compound of the invention can be acted upon by the enzyme at the surface of a tumor cell, resulting in the activation of pore-forming function. The compounds of the invention which are activated by metalloproteinases can be used to prevent vascularization of tumors. The process of active vascularization at a tumor site is associated with the secretion of specific proteases by tumor cells. These proteases can activate the pore-forming function of re-engineered inactive pore-forming agents of the invention, thereby preventing the vascularization process (which is required for growth and metastasis) or damaging tumor cells at the tumor site.

In another example, metal ions or chelating agents, e.g., ethylenediaminetetraacetic acid (EDTA), may be infused into the animal systemically or directly into the site of the target cell to activate or deactivate lytic function.

Lytic pore-forming activity can also be activated biochemically. Any substance secreted by or associated with an unwanted cell, such as an enzyme, e.g., protease, esterase, glycosidase, ectokinase, phosphatase, capable of acting upon the compound of the invention at the surface of the target cell, resulting in the activation of pore-forming function can be used. For example, certain re-engineered αHL overlap mutants are inactive until activated by cathepsin B which is secreted by certain tumor cells, e.g., melanoma cells.

BPNA

A prototype reagent for modifying peptides and proteins to make them photoactivatable has been developed. The water-soluble reagent, BPNA, places an α-carboxy-2-nitrobenzyl (CNB) group on sulfhydryl groups. This reagent can be used to produce modified polypeptides and proteins, e.g., pore-forming agents, derivatives of protein kinases and their peptide inhibitors.

BPNA can also be used to improve the synthesis of modified small molecules, e.g., sulfur-substituted analogs of biomolecules, e.g., ATPγS, GTPγS. In addition to modifying cysteine-containing proteins with BPNA, Cys-CNB can also be introduced into proteins by treating a chemically acylated suppressor tRNA with BPNA to make CNB-Cys-tRNA.

BPNA-modified polypeptides and proteins are activated or deprotected upon light exposure, e.g., near-UV light. To extend the wavelength of the absorption maximum of BPNA into the visible range, the chromophore can be altered (while retaining the 2-nitrobenzyl functionality), e.g., by adding methoxy or other groups to the benzene ring. Biological samples irradiated at longer wavelengths might suffer less direct and indirect (e.g. sensitized photooxidation) damage.

Since some proteins and polypeptides may be more difficult to inactivate than others, a more highly charged or more bulky sulfhydryl-directed protecting group based on the 2-nitrobenzyl functionality may be required. BPNA may be altered (while retaining the 2-nitrobenzyl functionality) consistent with these requirements. For example, the size of the protecting group may be increase by substituting the aromatic ring with an alkyl group. Alternatively, a large polymer, e.g., polyethylene glycol (PEG), can be linked to the aromatic ring to increase the size of the protecting group.

The reactivity of BPNA may also be altered by replacing the bromide leaving group with iodide or yet more reactive leaving groups.

The chiral center in BNPA that must yield diastereomeric cysteine adducts could also be a disadvantage in some circumstances and might be remedied without too much difficulty, e.g., by separating the R and S isomers of BPNA using a "chiral" HPLC column.

Modification of sulfhydryl groups with BPNA

Figure 12:
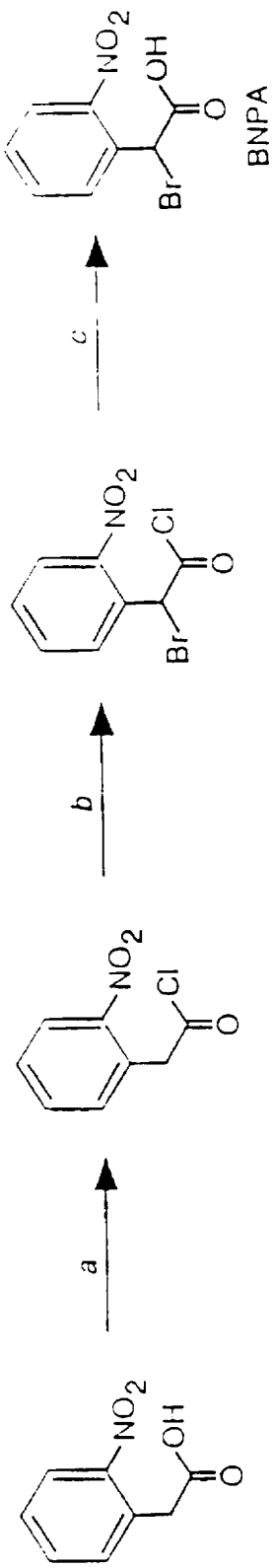
FIG. 12 is a diagram showing one-pot synthesis of 2-bromo-2-(2-nitrophenyl)acetic acid (BNPA). "a" represents SOCl$_2$ in CCl$_4$, 65° C., 1.5 hours; "b" represents N-bromosuccinimide/HBr, 70° C., 4.5 hours; and "c" represents ice water, 1 hour.

Known reagents for introducing photoremovable functional groups, e.g., 2-nitrobenzyl chloride, were found to be too insoluble in aqueous buffers to permit efficient modification of proteins and polypeptides under most circumstances. Therefore, BNPA was made and used to modify proteins and polypeptides by introducing a α-carboxy-2-nitrobenzyl (CNB) protecting group. BNPA can be produced in high yield by the bromination of 2-nitrophenylacetyl chloride, followed by hydrolysis of the acyl chloride group (see FIG. 12). BNPA is highly water-soluble at pH values around neutral. The α-carboxy group also increases the reactivity of the electrophilic center towards the cysteinate anion. Further, the presumed photoproduct, 2-nitrosoglyoxylic acid (FIG. 13), is less reactive than 2-nitrosobenzaldehyde. In addition, most proteins and polypeptides, particularly small peptides containing a CNB group, are more soluble in water than those protected with a simple 2-nitrobenzyl group.

Synthesis of BNPA α-halogenation of acyl chlorides was carried out according to methods known in the art, e.g., Harpp et al., *J. Org. Chem.*, 1975, 40:3420–27. To 2-(2-nitrophenyl)acetic acid (Aldrich, 5.0 g, 27.6 mmol), was added carbon tetrachloride (5 mL) and thionyl chloride (7.95 mL, 109 mmol). The mixture was stirred at 65° C. for 1.5 h to form the acyl chloride, after which N-bromosuccinimide (5.90 g, 33.1 mmol), CCl$_4$ (25 mL) and a catalytic amount (11 drops) of HBr in acetic acid were added to the flask. The mixture was then heated at 70° C. After 4.5 h, ice (25 g) was added to the cooled mixture, which was stirred vigorously for 1 h to hydrolyze the acyl chloride. The CCl$_4$ layer was retained and the aqueous phase was extracted with 3×25 mL CH$_2$Cl$_2$. The combined organic fractions were dried with Na$_2$SO$_4$ and the solvent was removed by evaporation, furnishing crude BNPA in near quantitative yield as a brown oil. A portion was recrystallized twice from CH$_2$Cl$_2$ yielding a buff solid. UV (10 mM NaP$_i$, pH 8.5): λmax=265 nm, ε4700, $^1$H NMR (CDCl$_3$): δ5.50 (1H, Br, COOH), 6.13 (1H, s), 7.55 (1H, m, aromatic), 7.71 (1H; m, aromatic), 8.02 (2H, m, aromatic).

Elemental analysis. Calculated for C$_9$H$_6$BrNO$_4$: C, 36.95; H, 2.33; Br, 30.73; N, 5.39; O, 24.61. Found: C, 37.35; H 2.48; Br, 27.59; N, 5.43: O, 24.98.

Therapeutic administration of re-engineered pore-forming agents

The compound of the invention can be administered to an animal, e.g., a human, suffering from a medical disorder e.g., cancer, or other conditions characterized by the presence of a class of unwanted cells. For example, therapeutic destruction of CD8-bearing T cells in HIV-infected patients may be efficacious in restoring a proper ratio of CD4 to CD8 cells in such patients (Rennie, Sci. Amer. 5/93:24–24).

The amount of compound administered will vary with the type of disease, extensiveness of the disease, and size of species of the animal suffering from the disease. Generally, amounts will be in the range of those used for other cytotoxic agents used in the treatment of cancer, although in certain instances lower amounts will be needed because of the increased specificity of the compound. The compound of the invention may be used in combination therapy in which the compound of the invention is administered either simultaneously or sequentially with a therapeutic agent which is not easily internalized by the target cell, such as cytotoxic chemotherapeutic agents, described above. For example, an oligomeric anti-sense DNA can be used to eliminate or down-regulate the expression of genes necessary for cell survival. Permeabilization of target cells by the compound of the invention can also facilitate the entry of ribozymes into the target cell, which can kill the cell by disrupting protein synthesis.

Generally, the compound of the invention will be administered by intravenous infusion, although it may also be administered subcutaneously or injected directly into site at which unwanted cells are to be destroyed, e.g. a tumor site. For example, inactive pore-forming agents which are activated by the enzymes endo C and clostripain can be administered to the patient first and allowed to bind to target cells; a second infusion of activating protease, e.g., endo C or clostripain, would then be administered to the patient to activate the bound pore-forming agent. To direct the activating protease to the target cell to be permeabilized or lysed, the activating protease may be linked to an antibody specific for the target cell.

The compound can also be aspirated to the tumor site via bronchial passages to treat cancers of the lung. Topical administration, e.g., in a cream formulation, to kill primary cancer cells such as skin cancers, can also be used and systemic administration via injections or implants is favored to kill metastatic cells. The compound of the invention can be combined with any non-toxic, pharmaceutically-acceptable carrier substance for administration to animals or humans.

The mutant activatable pore-forming agent of the invention which is not linked to a cell-specific ligand can be administered as described above. In this case, the specificity of the pore-forming agent is determined by the activating condition or substance, at the surface of the target cell. For example, a tumor-specific protease produced by a metastatic cancer cell can activate the lytic function of the inactive pore-forming agent, thus leading to the destruction of the cancer cell but not the destruction of a cell which does not produce the activating substance.

EXAMPLE 1

Protease-activated αHL

We will now describe a genetically-engineered lytic pore-forming agent which can be specifically activated by a protease.

αHL mutants

Mutants of αHL were generated from the plasmid pT7-NPH8S, which encodes the wild-type sequence of αHL as secreted by Staphylococcus aureus. pT7-NPH8S was made from pT7-NPH8 (Walker et al. J. Biol. Chem. 268:21782, 1992) by using oligonucleotide-directed mutagenesis to correct the mutation, Ser-217→Asn, that occurred during an earlier PCR. The codon Lys-8 in pT7-NPH8S was then changed to Ala by oligonucleotide-directed mutagenesis to eliminate an unwanted protease recognition site.

Truncated αHL genes were generated from the K8A gene by PCR using procedures described in Walker et al., supra. To obtain overlap mutant K8A,K131R(1-172●132-293), K8A,K131R was made from K8A by oligonucleotide-directed mutagenesis and then K8A,K131R1-172) was generated from K8A,K131R by PCR.

Coupled IVTT

Full length recombinant αHL (Walker et al., J. Biol. Chem. 267:10902–10909, 1992), truncated recombinant αHL polypeptides (Walker et al., J. Biol. Chem. 267:21782–21786, 1992), and recombinant two-chain complementary αHL polypeptides (Walker et al., J. Biol. Chem. 268:5285–5292) were then produced by IVTT according to methods known in the art by using an E. coli S30 extract (Promega No. L4500). The mix was supplemented with T7 RNA polymerase (NEB No. 251L, added at 2000 U/mL) and rifampicin (20 μg/mL) and ($^{35}$S) methionine. For hemolysis assays, the final methionine concentration in the IVTT mix was 0.5 mM (0.8 Ci/mmol) to ensure the synthesis of mutant polypeptides at concentrations in the range 10–50 μg/mL. Synthesis was carried out for 60 min. at 37° C. The integrity of the translation products and their relative concentrations were evaluated by SDS-PAGE and autoradiography.

Expression of recombinant proteins by bacteria, yeast, or other eucaryotic cells, using methods well-known in the art, is preferable for large-scale production of the compound. Thus, protease-activatable two-chain constructs of αHL were produced in E. coli using a bicistronic construct from which both chains are expressed in a single plasmid.

Hemolysis assay

To assay hemolysis in microtiter wells, IVTT extracts, untreated or treated with endo C were diluted 4-fold in well 1 (based on the mix volume before additions of protease etc.) in 20 mM K-phosphate, 150 mM NaCl, pH 7.4 containing 1 mg/mL bovine serum albumin (K-PBSA), and then subjected to two-fold serial dilutions in K-PBSA. Washed rabbit erythrocytes were then added to 0.5% and the plate was incubated at 20° C. In the spectrophotometric assay, hemolysis was monitored at room temperature (25° C.) by the decrease in light scattered at 600 nm after the addition of IVTT mix (10 μL) to rabbit erythrocytes diluted to 0.025% in K-PBSA (500 μL).

Proteolysis

Overlap mutants were activated by adding endo C (Promega No. V544A: 1 μg/1 μl in 25 mM NaH$_2$PO$_4$, 1 mM EDTA, pH 7.5) to the IVTT mix (10 μl). After 10 min. at 30° C., the protease was inactivated with TLCK (1 mM). For clostripain treatment, IVTT mix (10 μL) was incubated for 15 min. at 30° C. with enzyme (Sigma No. C-7403 0.1 μg) that had been activated in 50 mM Tris-HCl containing 2.5 mM DTT. Clostripain can also be inactivated with 1 mM TLCK.

Samples for electrophoresis were dissolved in 1× loading buffer, heated at 95° C. for 2 min., and subjected to electrophoresis in a 12% SDS-polyacrylamide gel (U.K. Laemmli, Nature 227:680, 1970). Radiolabelled markers (Gibco BRL) were ($^{14}$C)methylated proteins; myosin heavy chain ($M_r$=200,000); phosphorylase b ($M_r$=97,400); bovine serum albumin ($M_r$=68,000); ovalbumin ($M_r$=43,000); carbonic anhydrase ($M_r$=29,000); β-lactoglobulin ($M_r$=18,400); lysozyme ($M_r$=14,300).

Pore Formation

IVTT was carried out in the presence of ($^{35}$S)methionine (1200 Ci/mmol) and the reaction was stopped by the addition chloramphenicol (100 μM) and unlabelled methionine (5 mM), which prevent the incorporation of 35S into rabbit erythrocyte membrane proteins. IVTT mix (5 μL), untreated or treated with endo C (1 μg), was incubated with 10% rabbit erythrocytes (50 μL) for 60 min. at 20° C. in K-PBSA. The cells or membranes were recovered by centrifugation, dissolved in 30 μL 1× loading buffer (U.K. Laemmli, *Nature* 227:680, 1970), warmed at 45° C. for 5 min. and subjected to electrophoresis in a 12% SDS-polyacrylamide gel.

Characterization of αHL mutants

Staphylococcal α-hemolysin, a lytic pore-forming toxin, has been remodeled yielding inactive molecules that can be activated by Lys/Arg-directed proteases, which inactivate the wild-type protein. Wild type αHL polypeptides with nicks near the midpoint of the central glycine-rich loop (Walker et al., supra) are held together by a domain-domain interaction and are hemolytically active. By contrast, mutant αHL proteins comprising two αHL truncation mutants that overlap in the central loop (overlap mutants) have no or greatly reduced pore-forming activity. Overlap mutants have now been designed that are activated when redundant amino acids in the loop are removed by proteases.

Trypsin cleaves αHL after Lys-131 near the midpoint of the central loop (Walker et al., supra). However, wild-type αHL is inactivated by trypsin because of cleavage at a second site after Lys-8. The mutant αHL, K8A, in which Lys-8 was replaced with alanine, has the same hemolytic activity as the wild-type αHl, but is resistant to trypsin and related proteases.

Several overlap mutants were then generated from K8A by in vitro cotranslation of transcripts from two plasmids, each containing a truncated αHL gene. In all cases, the trypsin cleavage yielded the fragment combination, 1-131 and 132-293, which has strong hemolytic activity. Untreated overlap mutants were weakly active or inactive as determined by hemolysis assays and they were activated by the lysine- and arginine-directed trypsin or the lysine-directed endo C (FIGS. 1a–1c, FIGS. 2a–2d).

Mechanism of proteolytic activation

Figures 3A, 3B:
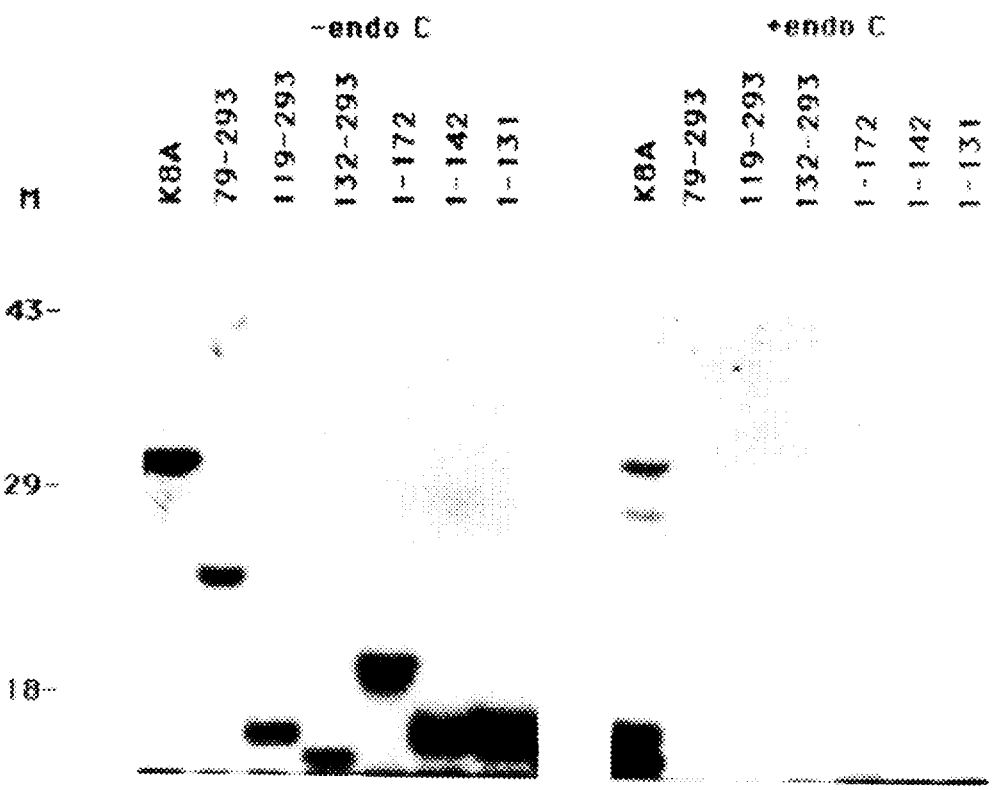
Figures 4A, 4B:
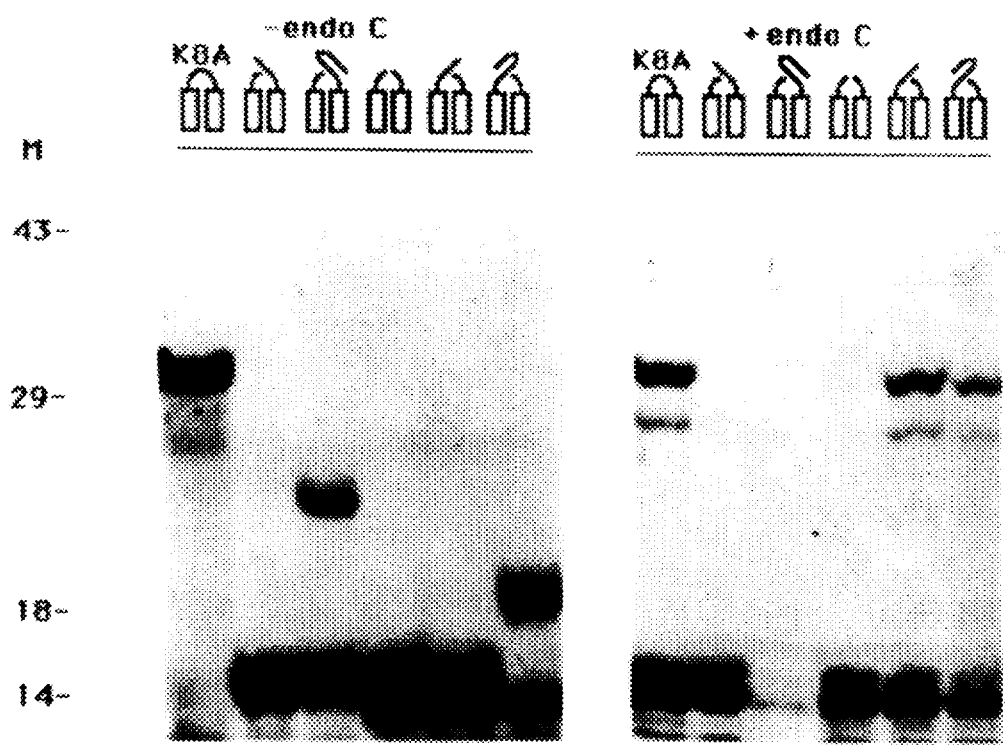
Figure 5:
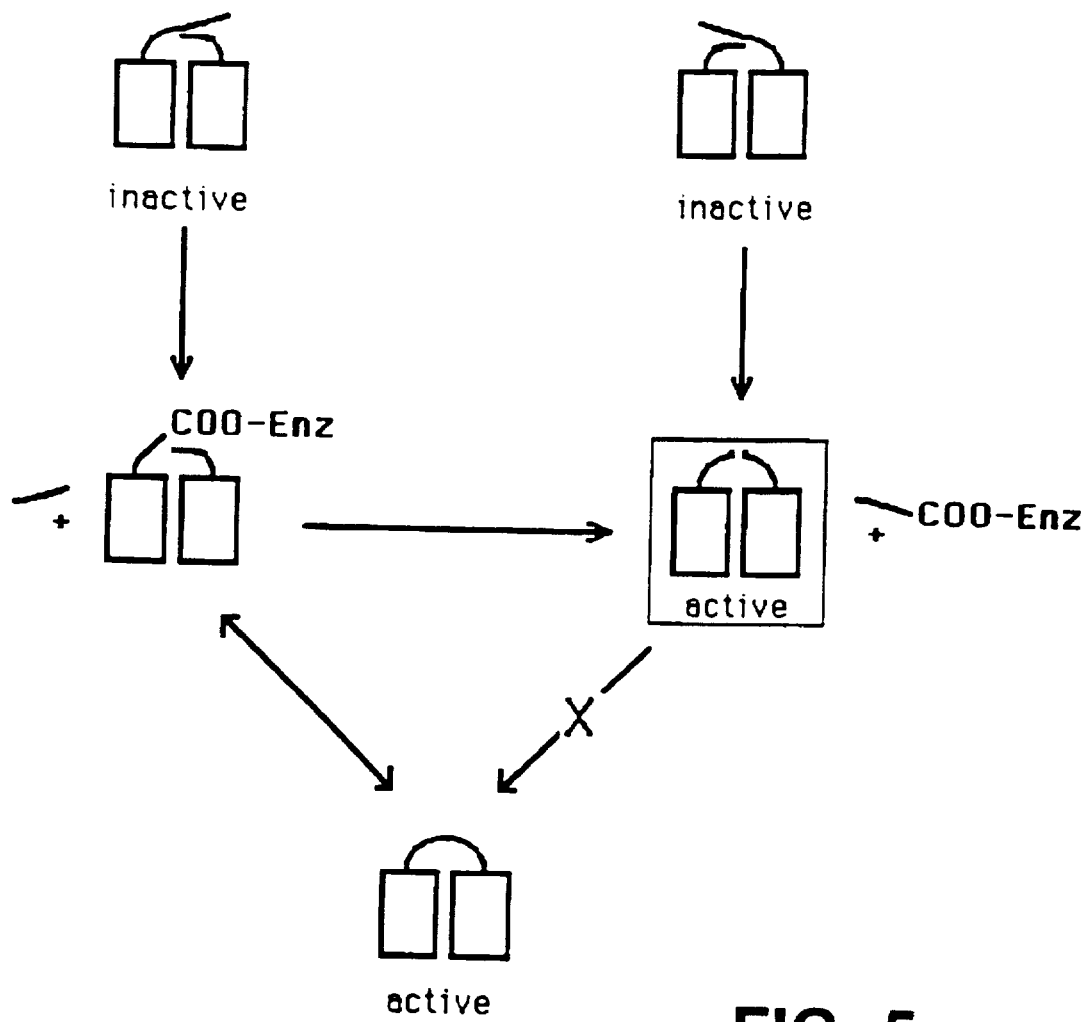
Figures 6A, 6B:
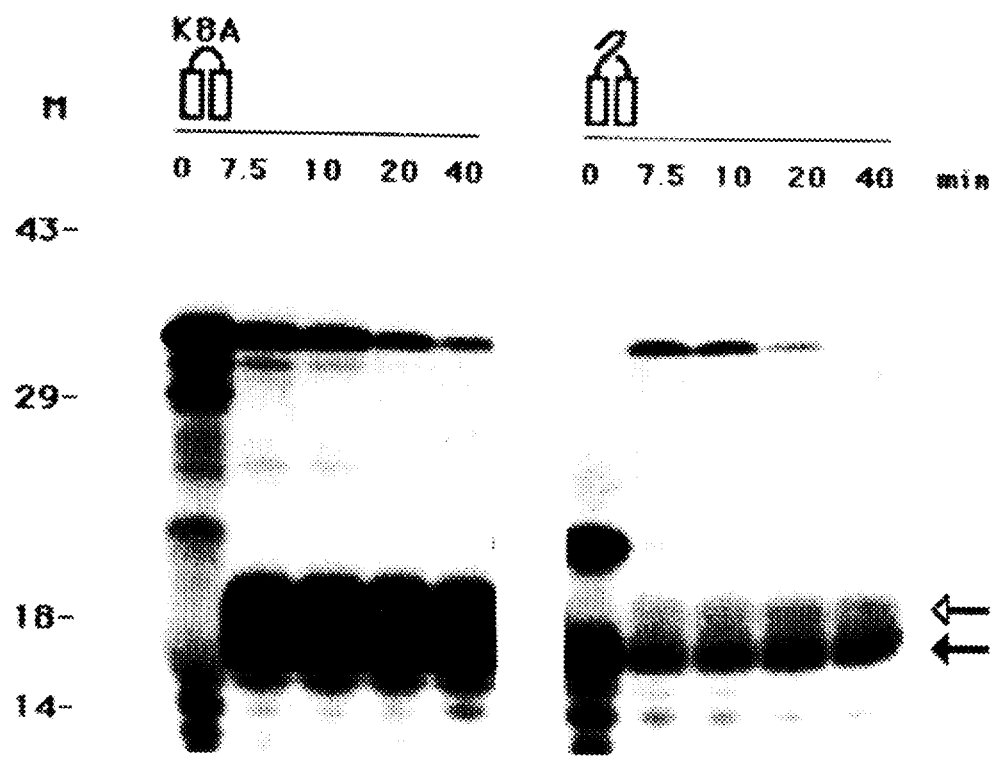

Overlap mutants and single polypeptide chains from which they were derived were cleaved with endo C. The single chains, encompassing large N-terminal or C-terminal fragments of αHL were rapidly digested into small peptides (FIGS. 3a and 3b). By contrast, when incorporated into overlap mutants, the same chains were converted to the fragments 1-131 and 132-293, but were otherwise resistant to the protease (FIGS. 4a and 4b). The full-length polypeptide generated by a transpeptidation reaction from forward overlap mutants (1-142●132-293 and 1-172●132-293: additional amino acids on the N-terminal polypeptide) can contain a normal peptide bond at the fusion site, because it is cleaved at the 131-132 bond upon further exposure to endo C (FIGS. 5, 6a, and 6b).

Selective activation by endo C and clostripain

Figure 7A:
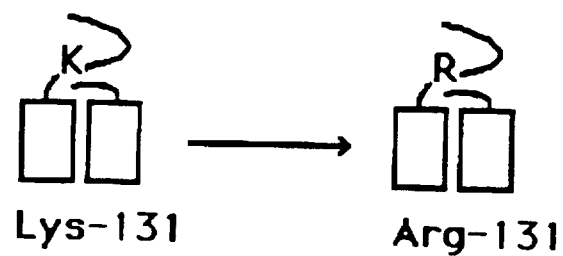
Figure 7B:
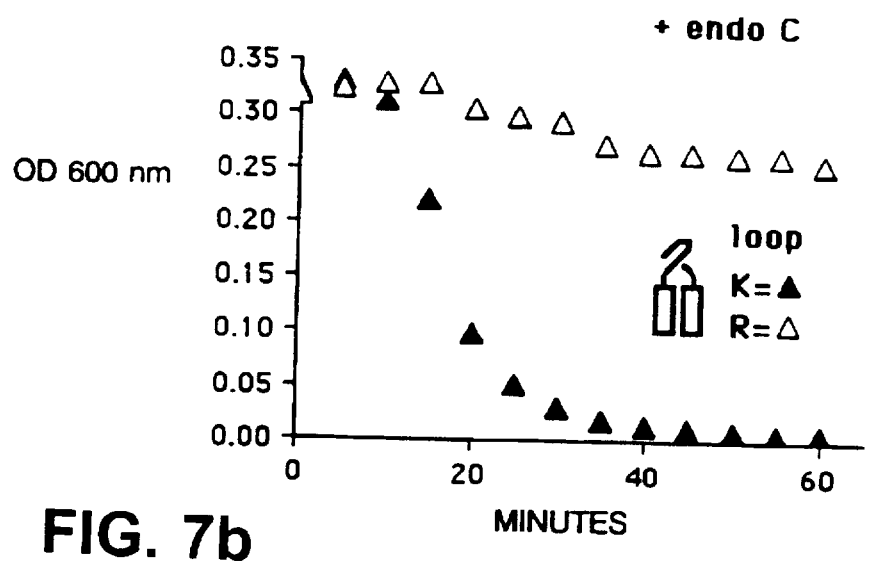
Figure 7C:
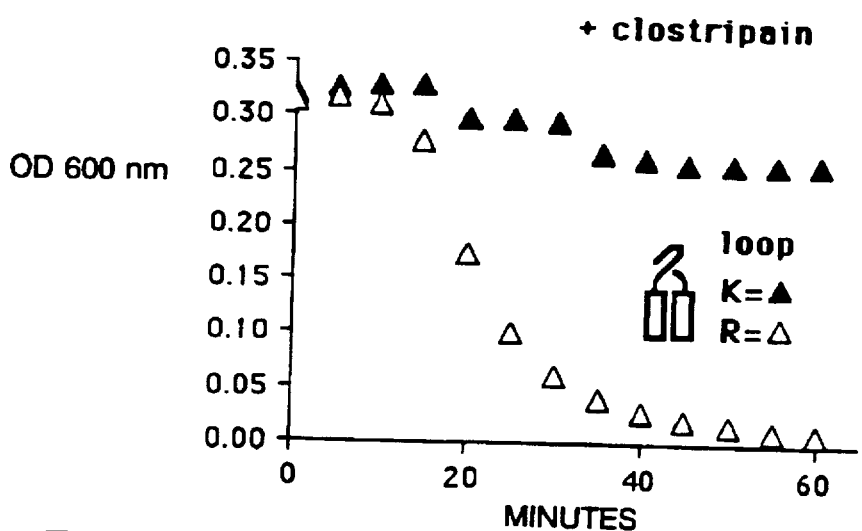

The requirement for protease specificity was tested by altering the recognition sequence in the central loop. Two overlap mutants, 1-142●132-293 and 1-172●132-293, were produced from the double point mutant K8A,K131R, and compared with the same overlap mutants generated from K8A. The Lys-131-containing mutants were selectively activated by the lysine-directed endo C and the Arg-131 mutants selectively activated by the arginine-directed clostripain (FIGS. 7a–7c).

Selective activation by cathepsin B

Two-chain constructs of αHL, 1-131●119-293 and 1-172●132-293 have been made for activation by the tumor protease, cathepsin B. Both constructs contain the following mutations: Lys 8→Ala, Gly130→Arg, and Lys 131→Arg. These re-engineered inactive αHL molecules were treated with cathepsin B in vitro. Activation was evaluated by: (1) analyzing the proteolytic cleavage products using SDS-PAGE; and (2) measuring the induction of lytic activity, i.e., lysis of rabbit erythrocytes. Data from these experiments indicate that these re-engineered αHL molecules are inactive until activated by cathepsin B.

Activation of these molecules can also be induced by treatment with tumor cell extracts, e.g., extracts of B16F10, a melanoma tumor cell line which secretes cathepsin B.

The inactive two-chain constructs of αHL can be further mutagenized and screened to identify mutants that are optimally activated by the activating protease, as described below.

EXAMPLE 2

Metal-responsive lytic pore-forming agents

We will now describe a mutant αHL which is responsive to metal ions.

Metal-ion sensitivity

Figure 8:
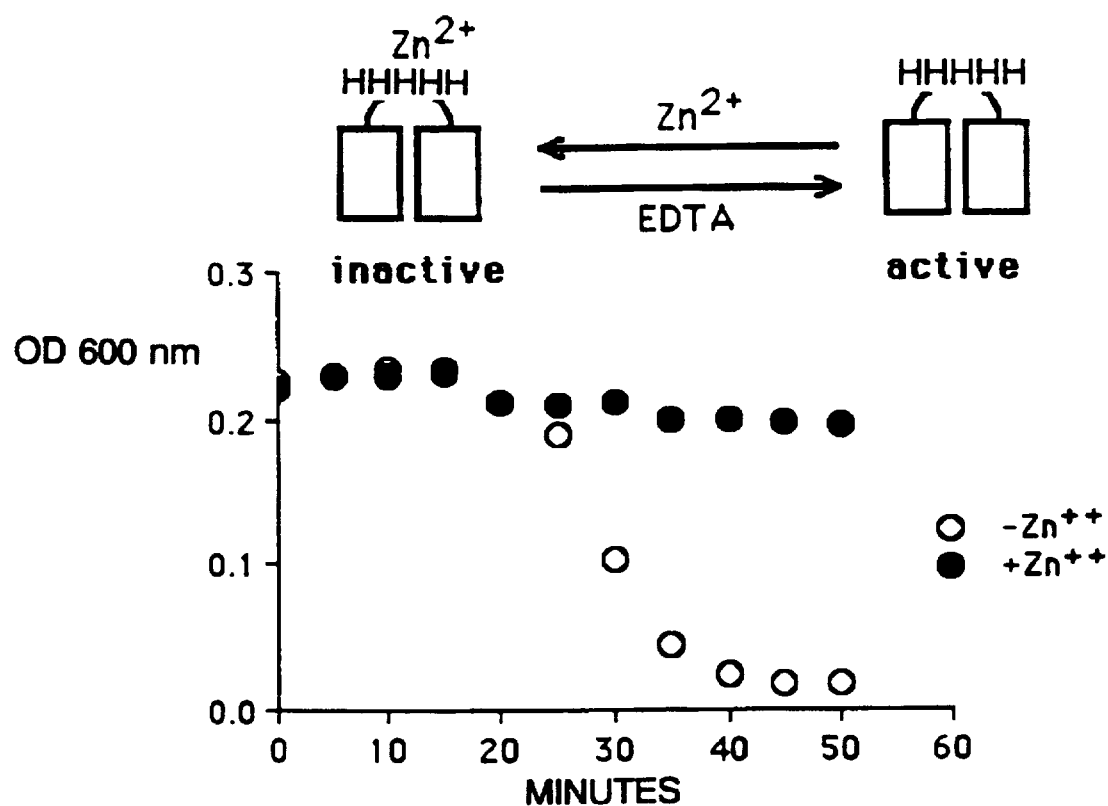
Figure 9:
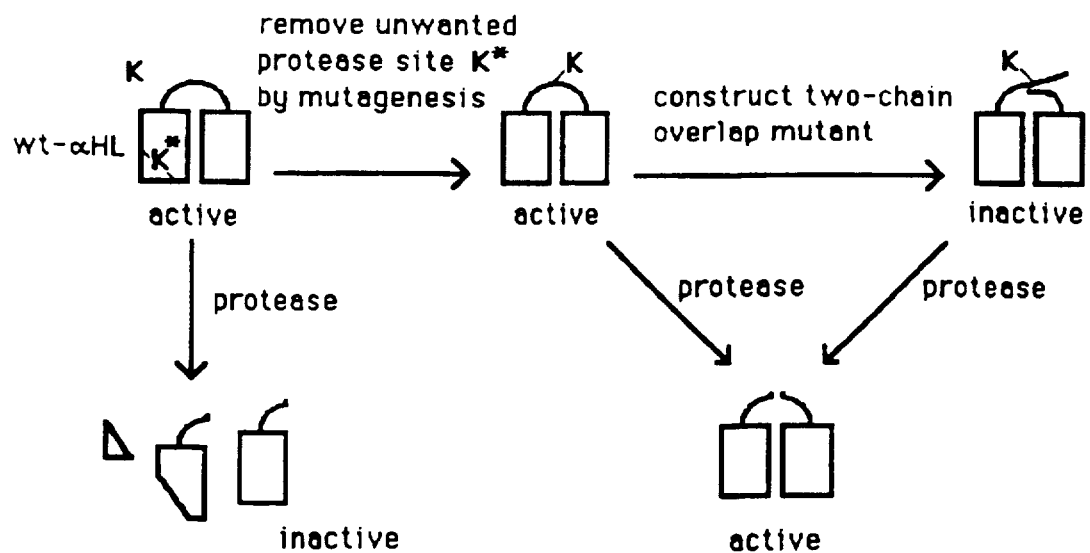
FIG. 9 is a diagram showing construction of a protease-activated mutant αHL from a protease-sensitive wild-type αHL.
Figure 10:
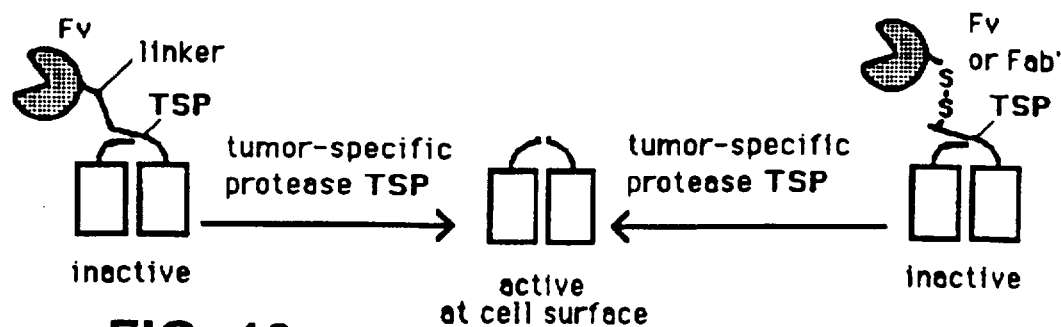
FIG. 10 is a diagram showing the structure of a chimeric compound of the invention in an inactive form and its structure after conversion to an active form by a tumor-specific protease.

A metal-sensitive αHL was produced by replacing residues 130-134 in the glycine-rich loop with five consecutive histidines. The hemolytic activity of this mutant, designated αHL-H5m, can be inactivated by $Zn^{2+}$ (10 μM) and reactivated with EDTA (2 mM), as shown in FIG. 8. In contrast, the wild type αHL is unaffected by $Zn^{2+}$ under the same conditions. Such metal-responsive agents can be inactivated by metals prior to administration to patients and activated in the patient by the administration of low levels of metal chelators, such as EDTA.

Lytic pore-forming agents which are activated by the presence of metal ions can also be used. Other metal-binding amino acids, such as cysteine and non-natural amino acids discussed above, can also be introduced into αHL to confer metal-ion sensitivity. Mutants which are activated or inactivated by other metal ions, such as divalent Group IIB and transition metals (Co, Ni, or Cu) can be identified using the screening assay of the invention, described below.

EXAMPLE 3

Photoactivatable lytic pore-forming agents

Photoactivatable pore-forming agents have been made by modifying αHL with 2-bromo-2-(nitrophenyl)acetic acid (BPNA). An active single-cysteine mutant of αHL was inactivated by reaction with BNPA. When the a-carboxy-2-nitrobenzyl (CNB) group, which is introduced by BNPA treatment, is removed by photolysis, pore-forming activity is restored. Photo-activatable pore-forming compounds can be activated while bound to the surface of the target cell. Pore-forming agents which can be photoactivated using the methods described below can be used for the permeabilization of selected cells in a collection of cells and for the permeabilization of a predetermined region of the surface of a single cell.

Modification of reduced glutathione (GSH) with BNPA

Stock solutions of the reduced form of glutathione (GSH, 100 mM in water) and BNPA (100 mM in 100 mM $NaP_i$, pH 8.5) were freshly made and used to prepare a reaction mixture containing 20 mM GSH, 20 mM BNPA in 250 mM $NaP_i$, pH 8.5, which was incubated overnight at room temperature in the dark. TLC (silica gel, system 1: ethanol, water, ammonia 7:2:1) revealed ~80% conversion of GSH to a new compound GS-CNB (Rf 0.70, ninhydrin positive, 254 nm absorbing). GSH (Rf 0.59, ninhydrin positive) and GSSG (oxidized GSH) almost comigrated in this system, but further analysis by system 3 (see below) revealed that the remainder of the GSH (~20%) had been oxidized to GSSG. GS-CNB was purified by preparative TLC (system 1) and isolated in 48% yield based on quantitative amino acid analysis (Hoogerheide et al., *Anal. Biochem.*, 1992, 201:146–51). UV (10 mM $NaP_i$, pH 8.5): $\lambda max=265$ nm, $\epsilon 4\,600$ (see FIG. 14).

Photolysis of GSH-CNB

GSH-CNB in water (2 mM, 42.5 µL) was buffered by the addition of 500 mM $NaP_i$ (5.0 µL) at either pH 6.0 or pH 8.5, followed by the addition of freshly prepared DTT solution (100 mM in water, 2.5 µL). The mixture was placed on ice in a microtiter plate well and photolyzed at 300 nm, 3.5 cm from a Fotodyne UV illuminator (Foto UV 300). Samples (6 µL) were removed at 0, 15, 30, 60, 90, and 120 min. and spotted onto a TLC plate, which was eluted with ethanol/water/ammonia (8:1:1, system 2) or isopropanol/2-butanol/acetic acid/water (5.0:5.0:2.6:3.5, system 3). Standards (Rf system 2, ninhydrin color; Rf system 3, ninhydrin color) were: GSH (0.20, pink; 0.22, red), GS-CNB (0.42, pink; 0.24, red) GSSG (oxidized GSH: 0.12, pink; 0.01, orange) and $GSO_3H$ (glutathionesulfonic acid: 0.30, pink; 0.13, orange). Under these conditions, the optimal release of GSH occurred after 30 min. of irradiation.

Synthesis of α-hemolysins by IVTT

In vitro synthesis of αHL polypeptides was carried out in an *E. coli* S30 extract supplemented with T7 RNA polymerase and rifampicin. 1.0 µg of plasmid DNA was added to a 25 µL reaction. The following mutant αHL genes were inserted into the plasmid pT7SflA (Walker et al., *J. Biol. Chem.*, 1992, 267:10902–909): K8A and S3C, H35C, and R104C. R104C was derived from K8A; S3C and H35C were derived from the unaltered αHL gene. K8A which has the properties of native αHL, but is less susceptible to inactivation by adventitious proteases was used as the WT-αHL control.

BNPA modification of single-cysteine mutants

αHL mutants (30 µL IVTT mix) were reduced for 5 min. at room temperature by the addition of 10 mM DTT (15 µL in water), 1.0M Tris.HCl, pH 8.5 (30 µL), and water (45 µL). 100 mM BNPA in 100 mM $NaP_i$, pH 8.5 (30 µL), was then added and the modification reactions were incubated at room temperature in the dark for 1 h (S3C) or 9 h (H35C, R104C). A mock reaction (K8A) was also incubated for 9 h. At the end of the reaction, excess BNPA and its low mass sulfhydryl adducts (e.g., with DTT) were removed by repeated cycles of dilution with 100 mM Tris.HCl (pH 6.0 or 8.5) and concentration by ultrafiltration (Amicon, Microcon 3). The final volume (135 µL) was readjusted to 150 µL with 100 mM Tris.HCl containing 10 mM DTT so that the concentration of DTT was 1 mM. The final concentration of BNPA and its low mass sulfhydryl adducts was ≤20 µM. The modified proteins were stored at −20° C. before use.

BNPA modification of staphylococcal αHL-R104C

αHL-R104C (0.36 mg/mL) was dialyzed against 10 mM Tris.HCl, pH 8.5, containing 5 mM β-ME. Dialyzed R104C (100 µL), 10 mM DTT in water (20 µL) and 1.0M Tris.HCl, pH 8.5 (40 µL) were incubated for 5 min. at room temperature before the addition of 100 mM BNPA in 100 mM $NaP_i$, pH 8.5 (40 µL). After 3 h at room temperature, 1.0M DTT (5 µL) was added and excess reagents were removed from the protein by gel filtration on Bio-Gel P-2 (Bio-Rad) eluted with 10 mM Tris.HCl, pH 8.5, containing 50 mM NaCl. A fraction was desalted and the buffer exchanged for 100 mM Tris.HCl, pH 8.5, 1.0 mM DTT by ultrafiltration (Amicon, Microcon-3).

Photolysis of CNB-αHL

CNB-αHL in 100 mM Tris.HCl (pH 6.0 or 8.5) containing 1 mM DTT (60, µL) was placed in a well of a 96-well microtiter plate and irradiated for 30 min. on ice through a 285 nm cut-off filter (Oriel, #51220) at 3.5 cm from a Foto UV 300 illuminator (Fotodyne). To assay for the unmasking of the protected cysteine residue, samples of the irradiated αHL polypeptides were treated with IASD and analyzed by SDS-PAGE. For the pH 8.5 sample, irradiated αHL (5 µL) was diluted with 100 mM Tris.HCl, pH 8.5 (3 µL), and reacted with 100 mM IASD in water (2 µL) for 1 h at room temperature. For the pH 6.0 sample, irradiated αHL (5 µL) was diluted with 1.0M Tris.HCl, pH 8.5 (2 µL) and water (1 µL) and treated in the same way.

Hemolysis assays

The lytic activity of the αHL polypeptides was measured by detecting lysis of rabbit erythrocytes in the presence of a test polypeptide. Unirradiated or irradiated CNB-αHL in 100 mM Tris.HCl, pH 8.5, containing 1 mM DTT (50, µL) was placed in a well of a 96-well flat-bottom plate and diluted with 20 mM $KP_i$, pH 7.4, 150 mM NaCl and 1 mg/mL BSA (K-PBSA) (50 µL). Two-fold serial dilutions were carried out with the same buffer. Washed rabbit erythrocytes were then added to 0.5% and the plate was incubated at 22° C. for 3 h. Hemolysis kinetics were recorded with a microplate reader (BioRad, Model 3550-UV).

Gel electrophoresis

SDS-PAGE was carried out according to Laemmli (Laemmli, *Nature*, 1970, 227:680–85) in 40 cm long 12% polyacrylamide gels run at constant 200 V for 40 h. Gels fixed in methanol/water/acetic acid (3:6:1) were dried and subjected to autoradiography or phosphorimager analysis. Prestained markers were from Gibco BRL.

Photodeprotection of a model tripeptide: CNB-glutathione

To test the efficacy of BNPA as a protecting agent for cysteines in peptides and proteins, the tripeptide glutathione (GSH, γ-Glu-Cys-Gly) was reacted with BNPA to form GS-CNB (γGlu-CysCNB-Gly). Purified GS-CNB was characterized by UV absorption spectroscopy (FIG. 14) and amino acid analysis (Hoogerheide et al., *Anal. Biochem.*, 1992, 201:146–51). When the protected peptide was irradiated at 300 nm in the presence of the reducing agent DTT (1 mM), GSH was released as determined by thin layer chromatography, amino acid analysis, and reaction with 5,5'-dithio(2-nitrobenzoic acid) (Ellman's reagent; used for the quantitation of sulfhydryl groups).

The photochemistry of 2-nitrobenzyl derivatives is highly dependent upon pH. In this case, a higher yield of GSH (~50%) was achieved when irradiation was carried out for the optimal time (e.g., 30 min.) at pH 6.0, rather than at pH 8.5 (~30%). Oxidation products of GSH, GSSG (oxidized GSH) and $GSO_3H$ (glutathionesulfonic acid), were not detected after 30 min. of irradiation.

Modification and photodeprotection of a model polypeptide: αHL-S3C

BNPA was used to selectively modify αHL with a single cysteine residue (αHL-S3C). After modification of the polypeptide, deprotection, i.e., removal of the CNB group, of αHL-S3C by near-UV light was evaluated. Prior to BNPA modification, gel-shift electrophoresis was used to determine sulfhydryl accessibility in single-cysteine mutants of αHL. Radiolabeled αHL polypeptides were modified with IASD and subjected to SDS-PAGE.

αHL-S3C was chosen as a model for studying polypeptide modification with BNPA because αHL-S3C undergoes a particularly large reduction in electrophoretic mobility upon modification with IASD (Krishnasastry et al., *FEBS Lett.*, 1994, 356:66–71), thus facilitating analysis. Reaction of radiolabeled αHL-S3C with BNPA was found to produce a substantial gel shift upon prolonged electrophoresis (FIG. 15, lane 3). Because the BPNA-shift is less pronounced, it is distinguishable from the shift produced by IASD (FIG. 15, lane 2).

Complete modification of αHL-S3C was achieved with 20 mM BNPA at pH 8.5 after 1 h at room temperature. Excess reagent was removed by repeated dilution and ultrafiltration. The modified hemolysin, αHL-S3C-CNB was then irradiated at pH 6.0 or pH 8.5 under conditions that had been previously established to give optimal release of GSH from GS-CNB. At pH 6.0, ~60% of the αHL-S3C-CNB was converted to a species that comigrated with αHL-S3C upon SDS-PAGE (FIG. 15, lane 4). This polypeptide contained a free sulfhydryl group as shown by reaction with IASD, which produced a large gel shift (FIG. 15, lane 5) of the same magnitude seen when unmodified αHL-S3C is treated with IASD (lane 2). When irradiation was performed at pH 8.5, far less αHL-S3C-CNB was converted to αHL-S3C and a polypeptide chain cleavage product that did not react with IASD (lane 7) was generated (FIG. 15, lane 6).

αHL-R104C-CNB: photoactivation of an inactive pore-forming agent

A single-cysteine mutant of αHL that would be inactivated by BNPA modification but reactivated upon irradiation was identified by screening 83 cysteine mutants. Of the 83 single-cysteine mutants identified, 22 mutants were suitable candidates for modification with BPNA based on their inactivation by covalent modification with IASD. Four mutants were eliminated because their cell surface binding was affected by the modification. Five mutants with cysteines in the central loop were also eliminated because, although they were inactivated by IASD, they were not inactivated by Ellman's reagent, which has structural features resembling the CNB group. Of the remaining 13, 9 were excluded because the cysteine mutation lowered the activity of the polypeptide slightly compared to wild-type αHL or because the IASD-modified protein showed some residual activity.

Four mutants (R104C, E111C, K168C, and D183C) were chosen for further study and development as photoactivatable inactive pore-forming agents. Representative experiments were carried out using αHL-R104C. Residue 104 is in a crucial region of the αHL polypeptide that both flanks the central loop and interacts with residues near the N terminus that cooperate with the loop in the final step of pore formation.

αHL-R104C is as active as WT-αHL before modification, and upon modification with IASD, gives an especially pronounced gel shift and has negligible activity. After treatment with BNPA, the pore-forming activity was again lost. The modification of αHL-R104C with BNPA and subsequent activation (deprotection) with near-UV irradiation was examined by SDS-PAGE, as described for αHL-S3C.

Important differences were seen between the behavior of αHL-R104C and αHL-H3C. Reaction with BNPA produced the expected decrease in electrophoretic mobility (FIG. 16, lane 3), but, at best, only 80% conversion to αHL-R104C-CNB was obtained. It appeared that unmodified αHLR104 remained after the reaction; however, close examination of the gels and treatment of the BNPA reaction products with IASD (FIG. 16, lane 4) revealed that there were two side-reaction products that migrated close to αHL-R104C, but contained no modifiable sulfhydryl groups. The same result was obtained with highly purified unlabeled R104C obtained by expression in *S. aureus*. Since these reaction products appeared to be devoid of hemolytic activity, the photochemistry of BNPA-modified αHL-R104C was examined.

BNPA-modified αHL-R104C was irradiated at 300 nm at pH 6.0 or pH 8.5. In contrast to αHL-S3C, more αHLR104C was generated at pH 8.5 than at pH 6.0 (FIG. 16, lanes 6 and 8), and chain cleavage to a product with $M_r$ ~30000 was less prevalent. The polypeptide presumed to be αHL-R104C was shifted to reduced mobility after treatment with IASD, demonstrating the presence of a free sulfhydryl group (FIG. 16, lanes 9 and 10). The large shift with IASD is highly characteristic of unmodified αHL-R104C. The two unidentified BNPA-modification products were unaffected by irradiation or subsequent treatment with IASD. Based on the amount of material that reacted with IASD, the yield of αHLR104C was ~60%. The pH-dependence of deprotection versus chain cleavage is the opposite to that seen with αHL-S3C and suggests that partitioning between the two reaction products depends on the environment provided by the folded polypeptide chain.

Photodeprotection of inactive αHL-R104C-CNB yields a functionally active hemolysin To determine whether the photoreleased αHL-R104C had pore-forming activity, hemolysis assays were performed with rabbit erythrocytes. WT-αHL that had been treated with BNPA was included as a control to determine whether UV irradiation decreased the activity of αHL. In a second control, αHL-H35C-CNB was included to demonstrate that photoproducts generated from components of the in vitro protein synthesis and chemical modification procedures do not cause lysis of rabbit erythrocytes.

WT-αHL had strong lytic activity before irradiation, while αHL-H35C-CNB and αHL-R104C-CNB were inactive (FIGS. 17–19, ○). After irradiation at 300 nm, WT-αHL retained its activity, while irradiated αHL-H35C-CNB remained inactive (FIGS. 17–19, ●). αHL-R104C-CNB was activated by irradiation (FIG. 19, ●). The extent of reactivation was 10–15% as determined by quantitative microtiter assays. By using αHLR104C-CNB made from unlabeled R104C obtained by expression in *S. aureus* which was available at higher concentrations and in high purity, appreciable lysis could be observed within a few minutes after photoactivation (FIG. 20).

Although the action of photoactivated αHL-R104C-CNB may be too slow (see FIGS. *7a–7c*) for certain applications such as the production of very rapid local transmembrane fluxes of $Ca^{2+}$, it is adequate for other applications. For example, αHL-R104C-CNB can be used to permeabilize cells to cause an exchange of small molecules, i.e., therapeutic agents which are about 2–3 kDa in size, across a cell membrane. Other lytic agents which create larger pores, e.g., aerolysin, perfringolysin, pneumolysin, streptolysin O, and listeriolysin, can be modified according to the invention to make photoactivatable pore-forming agents which can permeabilize cells with pores large enough to allow protein molecules to pass.

Since the removal of the 2-nitrobenzyl group from modified proteins or polypeptides is rapid, BPNA-modification can be used to make other photoactivatable pore-forming agents with different, i.e., faster, lysis kinetics. For example, lytic agents such as aerolysin, perfringolysin, pneumolysin, streptolysin O, listeriolysin, *Bacillus thuringensis* toxin, *E. coli*-derived hemolysin, *E. coli*-derived colicin, defensin, magainin, mellitin, complement, perforin, yeast killer toxin or histolysin, can be modified according to the invention to render them inactive until photoactivated to lytic activity. These data suggest that upon irradiation with near-UV light the inactive photoactivatable pore-forming agents of the invention are activated and permeabilize cell membranes. Water-soluble synthetic pore-forming compounds, e.g., lytic peptides or synthetic organic molecules, can also be modified using BPNA.

Applications and advantages of photoactivatable pore-forming agents

Photoactivatable pore-forming agents have potential applications in basic science and medicine. Bacterial pore-forming proteins, such as a-HL and streptolysin O, are important reagents in biology for the controlled permeabilization of cells. By using them, small molecules and even proteins can be introduced into or removed from the cell interior. Cell permeabilization has applications in many areas, e.g. in studies of cell signaling. One drawback of pore-forming agents is the lack of ability to control the activity of the agent. The invention solves this problem by providing inactive (but activatable) pore-forming compounds, e.g., a BPNA-modified α-HL that has been inactivated by site-directed mutagenesis and targeted chemical modification, the activity of which is controlled by light, i.e. lytic activity is photoactivatable.

Photoactivatable pore-forming agents may also be switched on-and-off, rather than merely triggered to lytic activity. One approach is to combine the photochemical trigger with another type of trigger for pore closure, e.g., photoactivated pores that are closed by low concentrations of divalent metal ions. For example, the metal-sensitive pore-forming agent, αHL-H5m, can be modified with BPNA. Pore forming activity of the resulting compound, αHL-H5m-CNB, can be activated by light, but the pores created in the cell can be closed by low concentrations of divalent metal ions.

Another approach is to use a photoisomerizable group for the targeted chemical modification of a key single cysteine. For example, spiropyrans, azobisbenzenes and related molecules have been used to produce switchable enzymes by random protein modification.

The modified α-hemolysin and other pore-forming agents modified according to the invention can be used for the permeabilization of one cell in a collection of cells (e.g. a neuron in a network) or one aspect of a single cell (e.g. the presynaptic terminus of a neuron). Other applications include nanostructure synthesis, e.g., two-dimensional arrays of pores with patterned open and closed states.

While rabbit erythrocytes undergo colloid osmotic lysis when treated with αHL, most other cells do not (Bhakdi et al., 1993, Med. Microbio. Immunol. 182:167–175). Hence, αHL-R104C-CNB and related BPNA-modified hemolysins can be used for cell permeabilization. Permeabilization with pore-forming agents compares favorably with other techniques for introducing molecules into cells, including microinjection and electroporation. The pore-forming agents of the invention have the advantages of being clinically useful, i.e., they can be delivered to remote areas of the body and activated, e.g., with a fiber optic device, and controllable, i.e., they can be triggered or switched on and off in vivo.

Since αHL binds irreversibly to membranes and is unlikely to diffuse from one cell to another, selective permeabilization of one cell in a collection of cells can be accomplished using photoactivatable αHL molecules, e.g., αHL-R104C-CNB. However once bound to a cell surface, αHL may diffuse on the surface of a cell. Surface-bound αHL diffusion will define the time interval for which permeabilization can be confined to one aspect of a cell, thereby allowing the exchange of reagents into defined regions of the interior. Since the effective activity of the pore would be greatly reduced by diffusional dilution, manipulation of this parameter represents one way of decreasing or shutting down activity.

The effective internal diameter of wild type αHL is 1-2 nm. Therefore, both macromolecules and organelles are retained by cells permeabilized with this reagent. In addition to α-HL, other pore-forming agents can be re-engineered according to the invention to make photoactivatable pore-forming agents which upon exposure to light create pore of varying sizes. For example, photoactivatable streptolysin can form membrane pores of greater than 30 nm in diameter. With this reagent, organelles are retained while many macromolecules, including IgG molecules and oligonucleotides, can pass through the pores.

Photoactivatable pore-forming agents of the invention also have applications in pharmacology, e.g., drug encapsulation. For example, drugs trapped in liposomes could be released at specific sites in the body by opening pores in the bilayers with light. These agents can also be used for cell or enzyme encapsulation. Encapsulated cells are useful for treating hormone deficiencies. Encapsulated enzymes can be used to treat diseases of metabolism. In both cases, the encapsulation system could be regulated by controlling access through the opening and closing of pores.

EXAMPLE 4

Photoactivation of non-pore-forming proteins and polypeptides

The properties of polypeptides other than pore-forming agents, e.g., enzymes and signal transduction molecules, can be extended by BNPA-modification. For example, BPNA-modified protein kinases can be used in studies of cell signaling. Such proteins can be photoactivated in a selected region of the cell such as the nucleus by using two-photon irradiation techniques, e.g., the technique of Denk, 1994, Proc. Natl. Acad. Sci. USA 91:6629–6633. Proteins, e.g., signal transduction proteins, which are activated by phosphorylation can be permanently activated with a thiophosphate group. The resulting thiophosphopeptides or proteins can then be modified with BPNA to render them photoactivatable.

Non-pore-forming proteins or polypeptides can be mutated using cysteine scanning mutagenesis as described above for αHL. Prior to BPNA-modification of cysteine mutants of αHL, pore-forming activity was examined before and after modification with the bulky, dianionic reagent IASD. Data from this study permitted the selection of potential candidate cysteine mutants that would likely be inactivated by the less drastic modification brought about by BNPA treatment. BNPA modification can be carried out directly on the large sets of cysteine mutants that are available for several polypeptides. The extent of IASD modification can be readily evaluated by charge-shift electrophoresis. Alternatively, since substantial gel shifts occur with BPNA-modified proteins and polypeptides, the effects of BPNA modification can be evaluated directly. If necessary, the extent of modification with BNPA can be determined by subsequent treatment with IASD.

The applications for caged peptides are numerous, e.g., the local release of enzyme inhibitors at specific sites within cells and the unmasking of peptides that block specific protein-protein interactions. BNPA can also be used to protect cysteines in peptides produced by chemical synthesis after they have been fully deprotected, as demonstrated by the modification of glutathione (described above) as well as to block cysteines or cysteine analogs that are placed in large synthetic peptides by chemical ligation. Unnatural amino acids with reactive sidechains introduced by chemical synthesis or site-specific modification can also be modified or protected with BNPA.

Photoactivatable peptides and proteins also have applications in pharmacology. Biologically active peptides and proteins could be released at specific sites in the body in predetermined doses and at defined times. Two photon activation may allow highly localized activation with radiation that is more penetrating than near-UV.

The procedure might also be extended to non-peptide biopolymers containing sulfhydryl groups and, in the absence of sulfhydryls, less reactive nucleophilic groups may be selectively modified. The gross physical characteristics of synthetic polymers modified at multiple sites with BNPA would be altered by photochemical deprotection. The loss of charge could be used to modulate those characteristics, e.g., the ability to penetrate biological membranes, or ion-exchange capacity.

Polypeptide chain cleavage by CysCNB

Polypeptide chains modified on cysteine with BNPA are cleaved when irradiation is carried out at pH values that are not optimal for deprotection (see FIG. 15). Photo-deprotection of BPNA-modified proteins or polypeptides at suboptimal pHs can be used to induce peptide cleavage, e.g., the cleavage of recombinant fusion proteins, the removal of synthetic peptides from solid supports, or the inactivation of polypeptides (such as enzymes) by chain cleavage.

EXAMPLE 5

αHL-Ab constructs

We will now describe a genetically-engineered inactive mutant of αHL linked to a target cell-specific antibody.

Construction of Ab-αHL conjugates

Any protease, which is specifically associated with a particular cell type, can be employed as an activator of inactive compounds of the invention, e.g., plasminogen activator, specifically urokinase-type plasminogen activator (uPA), which has been specifically associated with the metastatic phenotype of cancer cells (Liotta et al., Cell 64:327–336, 1991). The recognition sequence of plasminogen activator, Gly-Arg, or the same sequence preceded by a negatively charged amino acid, the recognition sequence for uPA, can be incorporated into the compound of the invention for the purpose of specific activation of the pore-forming agent. Similarly, the autocatalytic cleavage site for human collagenase IV (CIV) (Stetler-Stevenson et al., J. Biol. Chem. 264:1353–1356, 1989), can also be incorporated into the compound. These recognition sites can also serve as the basis for the semi-random combinatorial mutagenic cassette used in the generation of novel lytic pore-forming agents, described below.

Mutant two-chain αHL can be constructed as shown in FIG. 9. In the construct shown, the protease site for trypsin has been added. Since murine B16 melanoma cells have been shown to secrete plasminogen activator and collagenase IV (Reich et al. *Res.* 48:3307–3312, 1988; Wang et al., *Cancer Res.* 40:288–292, 1980), the protease cleavage sites for plasminogen activator and collagenase IV (gelatinase/ MMP2) (Stack et al. *Arch. Biochem. Biophys.* 287:240–249, 1991; Stack et al. *J. Biol. Chem.* 264:4277–4281, 1989; Harrison et al. *Anal. Biochem.* 180:110–113, 1989) can also be added for specific activation by this cell type. Linker regions can be glycine- and serine-rich peptides.

A reduced Fab fragment or an Fv fragment with an engineered cysteine can also be linked to an activated single-cysteine, two-chain mutant of αHL, as shown in FIG. 10. DNA encoding Fv fragments can be produced by RT-PCR of RNA extracted from antibody-producing hybridoma cells, such as those producing anti-dinitrophenol (DNP) or anti-B16 antibody (Chaudhary et al. *Acad. Sci. USA* 87:1066–1070, 1990). For in vitro screening purposes of chimeric compounds, the gene fusion approach is favored because sufficient two-chain compound can be obtained by IVTT. The two-chain construct can be expressed in bacteria using two different plasmids, a single plasmid with dual-promoters, or a single plasmid with a bicistronic operon. However, production of each component separately, followed by the joining of the antibody or other delivery agent, using chemical conjugation methodology described above, is favored for large-scale production.

Testing of conjugates in vitro (i) Activation by trypsin

An overlap mutant of αHL which is activated by trypsin is shown in FIG. 9. Such mutants and chimeric compounds containing such mutants can be activated in vitro by treatment with the protease, trypsin (trypsin site denoted by: K), inhibiting the protease, and assaying activation by hemolytic titer.

(ii) Activation by tumor proteases

B16-F10 melanoma cells (B16) (ATCC Accession No. CRL6475) can also be used as target cells. These highly metastatic cells secrete plasminogen activator and collagenase IV (Reich et al., supra; Wang et al., supra). Target cells can be lysed by activating antibody-PA-αHL (PA denotes the recognition sequence of the enzyme, plasminogen activator) and antibody-CIV-αHL (CIV denotes the recognition sequence of the enzyme, collagenase IV) in vitro, by using, as appropriate, plasminogen activator, collagenase IV and secretions from cells producing such enzymes.

Activation on the surface of target cells (i) Target cells; DNP-human erythrocytes Active wild type αHL efficiently lyses rabbit erythrocytes, which bear αHL receptors, but not human erythrocytes and other cells which do not bear receptors for αHL. The surfaces of human erythrocytes, which are resistant to αHL-mediated lysis, must first be modified with dinitrophenyl fluoride (DNP-F) to make them susceptible to lysis. The derivatized cells can then be treated with anti-DNP-K-αHL, washed, and then incubated with trypsin. In this example, the anti-DNP antibody serves to direct the compound to the derivatized target cells, resulting in increased local concentration of αHL polypeptides on the surface of cells which triggers the assembly of pores.

(ii) DNP-B16 melanoma cells

B16 melanoma cells can also be modified with DNP-F and then treated with anti-DNP-PA-αHL or anti-DNP-CIV-αHL. In this case, target cell viability can be assayed in vitro over 3 days by standard assays including trypan blue exclusion, $^{51}Cr$ release, $[^{35}S]$methionine uptake (protein synthesis) and $[^{3}H]$thymidine uptake (DNA replication) as an indication of the ability of the compound to permeabilize the target cells.

B16-specific antibody linked to αHL, e.g., anti-B16-PA-αHL or anti-B16-CIV-αHL, can be used to direct the compounds of the invention to the surface of B16 melanoma cells which have not been treated with DNP. Cell viability after incubation with the compound of the invention can be assayed as described above.

Selective permeabilization of target cells

Certain nucleated cells are often able to repair damage to the plasma membrane and might not be as readily disrupted as erythrocytes, however this limited permeabilization induced by the compound of the invention can be useful for the administration of therapeutic agents, which are normally poorly internalized by cells. For example, methotrexate-γ aspartate, an analog of the chemotherapeutic drug methotrexate, is normally non-toxic because of its inability to be internalized by cells but highly cytotoxic when it gains entry to the cytoplasm of a cell. Selective permeabilization of target cells can be used to facilitate the entry of this drug into tumor cells. Such a treatment strategy could minimize the side effects of chemotherapy, since the drug could only be taken up by permeabilized cells and would thus remain non-toxic to intact cells.

In another example, selective permeabilization of target cells can mediate a toxic influx of $Ca^{2+}$ into cells. Normally, intracellular $Ca^{2+}$ is maintained at a very low concentration (0.05–0.2 µM). Extracellular $Ca^{2+}$ levels are about four orders of magnitude greater (1.3 mM). Prolonged increases in intracellular free $Ca^{2+}$ can result in cell death and is thought to be the underlying mechanism of neuronal death in victims of stroke and neurodegenerative diseases (Randall et al., J. Neurosci. 12:1882–1895, 1992). Compounds of the invention can be used to direct $Ca^{2+}$-mediated killing to specific target cells by permeabilizing the target cells and permitting the influx of extracellular $Ca^2+$. Selective permeabilization of target cells can also be useful to facilitate the uptake of other cytotoxic agents, such as antisense oligonucleotide sequences or ribozymes.

EXAMPLE 5

Screens for activatable pore-forming lytic agents

A novel screening technique to identify lytic pore-forming agents which can be activated by cell-associated substances or conditions will now be described.

Protease site selection by combinatorial mutagenesis

A novel screening technique, based on combinatorial mutagenesis, has been devised for determining the peptide sequence specificity of proteases secreted by tumors and, at the same time, obtaining lytic pore-forming agents that are more rapidly and selectively activated by these proteases. These mutants can be then be used as cytotoxic agents against the same cells (FIG. 11). For example, mutant αHLs can be screened from combinatorial libraries on the basis of their ability to be activated by target cell extracts to lyse rabbit erythrocytes. A mutagenic cassette, containing random nucleic acid sequences generated by methods well known in the art, can be incorporated into the plasmid encoding the pore-forming agent. Since the aspects of the specificity of certain relevant proteases is known, the engineered protease sites encoded by the mutagenic cassette can be based on these sequences and need not be completely random.

For example, candidate clones from a combinatorial plasmid library can be plated on replicate nitrocellulose filters. The bacterial colonies on the filters are then lysed and recombinant proteins allowed to bind to the filters. One replicate filter is contacted with a cell extract of a target cell and as a control, a duplicate filter remains untreated. Both filters are exposed to blood agar plates and scored for the appearance of hemolytic plaques. Alternatively, the filters may be simultaneously contacted with cell extract and blood agar. The appearance of hemolysis on the plates containing filters which had been contacted with cell extract and the corresponding absence of hemolysis on plates containing untreated filters indicates that the candidate clone produces a hemolytic molecule that is activatable by a substance in the cell extract of the target cell. The screening process can be iterative in that a newly identified mutant can undergo further rounds of mutagenesis and screening as described above to identify mutants with improved activation capabilities.

For example, mutants of the αHL construct, K8A,G130R, K131R(1-131●119-293) with improved activation by the tumor protease, cathepsin B, have been identified using the combinatorial mutagenesis strategy described above. Four mutants were selected in a primary screen based on their ability to be activated by the arginine-specific protease, clostripain. The mutations were in the second chain of K8A,G130R,K131R(1-131●119-293) and spanned amino acids, 129-132 (see Table 1). In a second screen, one of the mutants containing the amino acids, Leu-Pro-Arg-Lys (SEQ ID NO:3) at positions 129-132, was found to be more rapidly activated by the tumor protease, cathepsin B, than the others. These data indicate that the screening assays of the invention can identify protease-activated pore-forming agents that are more rapidly and selectively activated by the activating proteases.

TABLE 1

| Residue: | 129 | 130 | 131 | 132 | |
|---|---|---|---|---|---|
| | Pro | Leu | Arg | Pro | (SEQ ID NO:1) |
| | Ser | Ile | Arg | Cys | (SEQ ID NO:2) |
| | Leu | Pro | Arg | Lys | (SEQ ID NO:3) |
| | Thr | Met | Arg | Val | (SEQ ID NO:4) |

Following the identification of a putatively positive colony, the plasmid can then be purified from the bacterial cells according to methods well-known in the art and analyzed to determine the DNA sequence of the mutagenic cassette. The candidate pore-forming compound can be expressed by IVTT and subjected to further analysis. The ability of the candidate pore-forming compound to be activated by the target cell can further be confirmed by incubating the translation product in the presence and absence of target cell extract, adding target cells, and assaying target cell lysis.

Selection of metal-sensitive mutants

A similar strategy using the screening assay of the invention can also be used to identify mutants with metal binding capabilities. As above, the screen can be based on a semi-random mutagenic cassette since complexity will be limited by using Cys or His codon-based oligonucleotides. As above, protein from bacterial colonies expressing αHL can be transferred to nitrocellulose filters in the presence and absence of metal ions. The duplicate filters are then placed in contact with blood agar plates and the blood agar plates scored for the appearance of hemolysis. The ability of metal ions to block or activate hemolysis can thus be evaluated.

Other embodiments are within the following claims.

---

What is claimed is:

1. An inactive staphylococcal α-toxin protein which is activated by exposure to light, wherein said protein is selected from the group consisting of R104C, E11C, K168C, and D183C.

2. The protein of claim 1, wherein said protein is R104C.

* * * * *